US011372000B2

(12) United States Patent
Hallermayer et al.

(10) Patent No.: US 11,372,000 B2
(45) Date of Patent: Jun. 28, 2022

(54) ANTIBODIES RECOGNIZING GENETIC VARIANTS OF NT-PROBNP

(71) Applicant: Roche Diagnostics Operations, Inc., Indianapolis, IN (US)

(72) Inventors: Klaus Hallermayer, Feldafing (DE); Monika Soukupova, Wessobrunn (DE); Christina Porzig, Antdorf (DE); Ulrike Kurtkaya, Graefelfing (DE); Leopold Von Proff, Hohenspeissenberg (DE); Sonja Fiesel, Penzberg (DE); Marion Herrmann, Penzberg (DE); Stefanie Kern, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 69 days.

(21) Appl. No.: 16/538,886

(22) Filed: Aug. 13, 2019

(65) Prior Publication Data
US 2019/0369117 A1 Dec. 5, 2019

Related U.S. Application Data

(63) Continuation of application No. PCT/EP2018/053474, filed on Feb. 13, 2018.

(30) Foreign Application Priority Data

Feb. 13, 2017 (EP) .................................... 17155810

(51) Int. Cl.
| C07K 16/26 | (2006.01) |
| A61K 39/395 | (2006.01) |
| G01N 33/68 | (2006.01) |
| C07K 14/575 | (2006.01) |
| C07K 14/58 | (2006.01) |

(52) U.S. Cl.
CPC ..... G01N 33/6854 (2013.01); A61K 39/3955 (2013.01); C07K 16/26 (2013.01); G01N 33/6857 (2013.01); C07K 14/575 (2013.01); C07K 14/58 (2013.01); C07K 2317/20 (2013.01); C07K 2317/33 (2013.01); C07K 2317/34 (2013.01); C07K 2317/40 (2013.01); C07K 2317/565 (2013.01); C07K 2317/76 (2013.01); C07K 2317/92 (2013.01); C07K 2317/94 (2013.01); G01N 2333/58 (2013.01); G01N 2800/325 (2013.01)

(58) Field of Classification Search
CPC ... C07K 14/575; C07K 16/26; A61K 39/3955
See application file for complete search history.

(56) References Cited

U.S. PATENT DOCUMENTS

2014/0256915 A1  9/2014  Schraeml et al.

FOREIGN PATENT DOCUMENTS

| JP | 2007-535470 A | 12/2007 |
| JP | 2010-11860 A | 1/2010 |
| JP | 2011-528115 A | 11/2011 |
| JP | 2013-505437 A | 2/2013 |
| WO | 2002/083913 A1 | 10/2002 |
| WO | 2002/089657 A2 | 11/2002 |
| WO | 2004099252 A1 | 11/2004 |
| WO | 2004099253 A1 | 11/2004 |
| WO | 2009/066010 A1 | 5/2009 |
| WO | 2010007041 A1 | 1/2010 |
| WO | 2011033034 A1 | 3/2011 |

OTHER PUBLICATIONS

Ferrara etal (2015. mAbs. 7(1): 32-41).*
ASHG 2015 Abstracts, p. 76 (159).
Bonow, Robert O., New Insights Into the Cardiac Natriuretic Peptides, Circulation, 1996, pp. 1946-1950, vol. 93.
Clerico, Aldo et al., State of the art of immunoassay methods for B-type natriuretic peptides: An update, Critical Reviews in Clinical Laboratory Science, 2015, pp. 56-69, vol. 52, No. 2.
Foo, Jared Yong Yang et al., Circulation Fragments of N-Terminal Pro-B-Type Natriuretic Peptides in Plasma of Heart Failure Patients, Clinical Chemistry, 2013, pp. 1523-1531, vol. 59, No. 10.
International Search Report dated Mar. 29, 2018, in Application No. PCT/EP2018/053474, 3 pp.
Köhler, G. and Milstein, C., Continuous cultures of fused cells secreting antibody of predefined specificity, Nature 1975, pp. 495-497, vol. 256.
Lee, Yujean et al., An antibody reactive to the Gly63-Lys68 epitope of NT-proBNP exhibits O-glycosylation-independent binding, Experimental & Molecular Medicine, 2014, e114, 9 pp., vol. 46, No. 9.
Lefranc, Marie-Paule, IMGT, the International ImMunoGeneTics Information System, Cold Spring Harbor Protocol, 2011, 8 pp., doi:10.1101/pdg.top115.
Mueller, Thomas et al., Long-term stability of endogenous B-type natriuretic peptide (BNP) and amino terminal proBNP (NT-proBNP) in frozen plasma samples, Clinical Chemistry & Laboratory Medicine, 2004, pp. 942-944, vol. 42, No. 8.
Prontera, Concetta et al.. Comparison between analytical performances of polyclonal and monoclonal electrochemiluminescence immunoassays for NT-proBNP, Clinica Chimica Acta, 2009, pp. 70-73, vol. 400.

(Continued)

*Primary Examiner* — Zachary C Howard
(74) *Attorney, Agent, or Firm* — Stinson LLP

(57) ABSTRACT

The present disclosure relates to an antibody that specifically binds a mutated NT-proBNP having i) a mutation substituting arginine at position 46 with histidine or ii) a mutation substituting glutamic acid at position 43 with aspartic acid. Moreover, the present disclosure relates to a mutated NT-proBNP or fragment thereof. Further, envisaged by the present disclosure are kits containing the antibody of the present disclosure, or the mutated NT-proBNP of the present disclosure. The present disclosure also concerns a method for diagnosing heart failure.

13 Claims, 6 Drawing Sheets

Specification includes a Sequence Listing.

(56) References Cited

OTHER PUBLICATIONS

Saenger, Amy K. et al., Specificity of B-Type Natriuretic Peptide Assays: Cross-Reactivity with Different BNP, NT-proBNP, and proBNP Peptides, Clinical Chemistry, 2017, pp. 351-358, vol. 63, No. 1.
Wu, Alan H. B. et al., Analytical and Clinical Evaluation of the Bayer ADVIA Centaur Automated B-Type Natriuretic Peptide Assay in Patients with Heart Failure: A Multisite Study, Clinical Chemistry, 2004, pp. 867-873, vol. 50, No. 5.
Yates, Andrew et al., Ensembl 2016, Nucleic Acids Research, 2016, pp. D710-D716, vol. 44.
DbSNP Cluster ID rs74613227 Homo Sapiens, National Institute of Health, 2020, 1 p.
DbSNP Custer ID rs61761991 Homo Sapiens, National Institute of Health, 2020, 1 p.

\* cited by examiner

NT-proBNP (aa 1-76):

NT-proBNP (aa 27-102):

NT-proBNP E69D:

S-23.4.66 rS-22.2.195

NT-proBNP R72H:

S-23.4.66 rS-22.2.195

SEQUENCE LISTING

<160> NUMBER OF SEQ ID NOS: 30

<210> SEQ ID NO 1
<211> LENGTH: 76
<212> TYPE: PRT
<213> ORGANISM: Homo sapiens
<220> FEATURE:
<223> OTHER INFORMATION: NT-proBNP with R46H mutation

<400> SEQUENCE: 1

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro His Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg
65                  70                  75

<210> SEQ ID NO 2
<211> LENGTH: 76
<212> TYPE: PRT
<213> ORGANISM: Homo sapiens
<220> FEATURE:

-continued

<223> OTHER INFORMATION: NT-proBNP with E43D mutation

<400> SEQUENCE: 2

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Asp Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg
65                  70                  75

<210> SEQ ID NO 3
<211> LENGTH: 76
<212> TYPE: PRT
<213> ORGANISM: Homo sapiens
<220> FEATURE:
<223> OTHER INFORMATION: wild-type NT-proBNP

<400> SEQUENCE: 3

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg
65                  70                  75

<210> SEQ ID NO 4
<211> LENGTH: 212
<212> TYPE: PRT
<213> ORGANISM: Artificial Sequence
<220> FEATURE:
<223> OTHER INFORMATION: light chain of antibody S-22.2.195

<400> SEQUENCE: 4

Tyr Glu Leu Thr Gln Pro Thr Ser Val Ser Val Ala Leu Glu Gln Thr
1               5                   10                  15

Ala Glu Ile Thr Cys Gln Gly Asp Leu Leu Asp Asp Ala Tyr Val Ala
            20                  25                  30

Trp Tyr Gln Gln Lys Pro Gly Gln Ala Pro Met Lys Leu Ile Tyr Lys
        35                  40                  45

Asp Ser Glu Arg Pro Ser Gly Ile Leu Asp Arg Phe Ser Gly Ser Ser
    50                  55                  60

Ser Gly Lys Ile Ala Thr Leu Ile Ile Ser Gly Ala Arg Thr Glu Asp
65                  70                  75                  80

Glu Ala Asp Tyr Tyr Cys Leu Ser Val Asp Ser Ser Glu Tyr Ser Val
                85                  90                  95

Phe Gly Ser Gly Thr Arg Leu Thr Val Leu Ser Gln Pro Lys Ser Ala
            100                 105                 110

Pro Ser Val Thr Leu Phe Pro Pro Ser Lys Glu Glu Leu Asp Thr Asn
        115                 120                 125

Lys Ala Thr Val Val Cys Leu Ile Ser Asp Phe Tyr Pro Gly Ser Val

```
                130                 135                 140
Asn Val Val Trp Lys Ala Asp Gly Ser Thr Ile Asn Gln Asn Val Lys
145                 150                 155                 160

Thr Thr Gln Ala Ser Lys Gln Ser Asn Ser Lys Tyr Ala Ala Ser Ser
                165                 170                 175

Tyr Leu Thr Leu Thr Gly Ser Glu Trp Lys Ser Lys Ser Tyr Thr
                180                 185                 190

Cys Glu Val Thr His Glu Gly Ser Thr Val Lys Thr Val Lys Pro
                195                 200                 205

Ser Glu Cys Ser
    210

<210> SEQ ID NO 5
<211> LENGTH: 450
<212> TYPE: PRT
<213> ORGANISM: Artificial Sequence
<220> FEATURE:
<223> OTHER INFORMATION: heavy chain of antibody S-22.2.195

<400> SEQUENCE: 5

Gln Val Arg Leu Gln Glu Ser Gly Pro Ser Leu Val Lys Pro Ser Gln
1               5                   10                  15

Thr Leu Ser Leu Thr Cys Thr Val Ser Gly Phe Ser Leu Ile Gly Glu
                20                  25                  30

Tyr Val Thr Trp Val Arg Gln Ala Pro Gly Lys Ala Pro Glu Trp Leu
                35                  40                  45

Ser Thr Met Ala Ser Gly Gly Thr Ile Phe Tyr Asn Pro Thr Leu Lys
50                  55                  60

Ala Arg Leu Ser Ile Thr Lys Asp Ser Thr Lys Ser Gln Phe Ser Leu
65                  70                  75                  80

Ser Val Ser Ser Val Thr Ser Glu Asp Thr Ala Met Tyr Tyr Cys Val
                85                  90                  95

Arg Ser Ser Val Ser Pro Gly Asp Asp Arg Asp Val Trp Gly Arg Gly
                100                 105                 110

Leu Leu Val Thr Val Ser Ser Ala Ser Thr Thr Pro Pro Lys Val Tyr
                115                 120                 125

Pro Leu Thr Ser Cys Cys Gly Asp Thr Ser Ser Ser Ile Val Thr Leu
                130                 135                 140

Gly Cys Leu Val Ser Ser Tyr Met Pro Glu Pro Val Thr Val Thr Trp
145                 150                 155                 160

Asn Ser Gly Ala Leu Thr Ser Gly Val His Thr Phe Pro Ala Ile Leu
                165                 170                 175

Gln Ser Ser Gly Leu Tyr Ser Leu Ser Ser Val Val Thr Val Pro Ala
                180                 185                 190

Ser Thr Ser Gly Ala Gln Thr Phe Ile Cys Asn Val Ala His Pro Ala
                195                 200                 205

Ser Ser Thr Lys Val Asp Lys Arg Val Glu Pro Gly Cys Pro Asp Pro
                210                 215                 220

Cys Lys His Cys Arg Cys Pro Pro Glu Leu Pro Gly Gly Pro Ser
225                 230                 235                 240

Val Phe Ile Phe Pro Pro Lys Pro Lys Asp Thr Leu Thr Ile Ser Gly
                245                 250                 255

Thr Pro Glu Val Thr Cys Val Val Asp Val Gly Gln Asp Asp Pro
                260                 265                 270

Glu Val Gln Phe Ser Trp Phe Val Asp Asn Val Glu Val Arg Thr Ala
```

```
                275                 280                 285

Arg Thr Lys Pro Arg Glu Glu Gln Phe Asn Ser Thr Phe Arg Val Val
    290                 295                 300

Ser Ala Leu Pro Ile Gln His Gln Asp Trp Thr Gly Gly Lys Glu Phe
305                 310                 315                 320

Lys Cys Lys Val His Asn Glu Gly Leu Pro Ala Pro Ile Val Arg Thr
                325                 330                 335

Ile Ser Arg Thr Lys Gly Gln Ala Arg Glu Pro Gln Val Tyr Val Leu
            340                 345                 350

Ala Pro Pro Gln Glu Glu Leu Ser Lys Ser Thr Leu Ser Val Thr Cys
        355                 360                 365

Leu Val Thr Gly Phe Tyr Pro Asp Tyr Ile Ala Val Glu Trp Gln Lys
    370                 375                 380

Asn Gly Gln Pro Glu Ser Glu Asp Lys Tyr Gly Thr Thr Thr Ser Gln
385                 390                 395                 400

Leu Asp Ala Asp Gly Ser Tyr Phe Leu Tyr Ser Arg Leu Arg Val Asp
                405                 410                 415

Lys Asn Ser Trp Gln Glu Gly Asp Thr Tyr Ala Cys Val Val Met His
            420                 425                 430

Glu Ala Leu His Asn His Tyr Thr Gln Lys Ser Ile Ser Lys Pro Pro
        435                 440                 445

Gly Lys
    450

<210> SEQ ID NO 6
<211> LENGTH: 7
<212> TYPE: PRT
<213> ORGANISM: Artificial Sequence
<220> FEATURE:
<223> OTHER INFORMATION: fragment of NT-proBNP with R46H mutation

<400> SEQUENCE: 6

Glu Ser Pro His Pro Thr Gly
1               5

<210> SEQ ID NO 7
<211> LENGTH: 10
<212> TYPE: PRT
<213> ORGANISM: Artificial Sequence
<220> FEATURE:
<223> OTHER INFORMATION: fragment of NT-proBNP with R46H mutation

<400> SEQUENCE: 7

Gln Glu Ser Pro His Pro Thr Gly Val Trp
1               5                   10

<210> SEQ ID NO 8
<211> LENGTH: 7
<212> TYPE: PRT
<213> ORGANISM: Artificial Sequence
<220> FEATURE:
<223> OTHER INFORMATION: fragment of NT-proBNP with E43D mutation

<400> SEQUENCE: 8

Pro Leu Gln Asp Ser Pro Arg
1               5

<210> SEQ ID NO 9
<211> LENGTH: 10
<212> TYPE: PRT
<213> ORGANISM: Artificial Sequence
```

<220> FEATURE:
<223> OTHER INFORMATION: fragment of NT-proBNP with E43D mutation

<400> SEQUENCE: 9

Glu Pro Leu Gln Asp Ser Pro Arg Pro Thr
1               5                   10

<210> SEQ ID NO 10
<211> LENGTH: 636
<212> TYPE: DNA
<213> ORGANISM: Artificial Sequence
<220> FEATURE:
<223> OTHER INFORMATION: nucleic acid sequence for light chain of
      antibody S-22.2.195

<400> SEQUENCE: 10

```
tatgaactga cccagccgac ttcagtgtcg gtggccttgg aacagacggc cgaaatcacc    60
tgccagggag atttgttgga tgatgcatat gtggcttggt accagcagaa gccgggccag   120
gctccgatga aactcattta taaagacagt gagcggcctt cagggatcct tgaccggttc   180
tctggctcca gctcaggcaa aatagccacc ctaatcatca gcggggcccg gaccgaggac   240
gaggccgact attactgtct gtcagttgac agcagcgaat attctgtttt cggcagcggg   300
accaggttga ccgttttgag tcagcccaag tccgcaccct cggtcaccct gttcccgcct   360
tccaaggagg agctcgatac caacaaggcc accgtggtgt gtctcatcag cgacttctac   420
ccgggtagcg tgaacgtggt ctggaaggca gatggcagca ccatcaatca gaacgtgaag   480
accacccagg cctccaaaca gagcaacagc aagtacgcgg ccagcagcta cctgaccctg   540
acgggcagcg agtggaagtc taagagcagt tacacctgcg aggtcacgca cgaggggagc   600
accgtgacga agacagtgaa gccctcagag tgttct                             636
```

<210> SEQ ID NO 11
<211> LENGTH: 1350
<212> TYPE: DNA
<213> ORGANISM: Artificial Sequence
<220> FEATURE:
<223> OTHER INFORMATION: nucleic acid sequence for heavy chain of
      antibody S-22.2.195

<400> SEQUENCE: 11

```
caggtgcggc tgcaggagtc gggacccagc ctggtgaagc cctcacagac cctctccctc    60
acctgcacgg tctctggatt ctcattaatc ggcgagtatg taacctgggt ccgccaggct   120
ccaggaaagg cgccggagtg gctgagtacg atggccagtg gtggaaccat attttataat   180
ccgaccctga aggcccgact cagcatcacc aaggacagca ccaagagcca attctccctg   240
tcagtgagca gcgtgacatc tgaggacacg gccatgtatt actgtgtaag atcttccgtt   300
tcaccgggcg atgatagaga tgtctggggc cgaggactcc tggttaccgt ctcctcggcc   360
tccaccacac ccccgaaagt ctaccctctg acttcttgct gcggggacac gtccagctcc   420
atcgtgaccc tgggctgcct ggtctccagc tatatgcccg agccggtgac cgtgacctgg   480
aactctggtg ccctgaccag cggcgtgcac accttcccgg ccatcctgca gtcctccggg   540
ctctactctc tcagcagcgt ggtgaccgtg ccggccagca cctcaggagc cagaccttc    600
atctgcaacg tagcccaccc ggccagcagc accaaggtgg acaagcgtgt tgagcccgga   660
tgcccggacc catgcaaaca ttgccgatgc ccaccccctg agctcccgg aggaccgtct   720
gtcttcatct tccccgaa acccaaggac accttacaa tctctggaac gcccgaggtc   780
acgtgtgtgg tggtggacgt gggccaggat gaccccgagg tgcagttctc ctggttcgtg   840
```

```
gacaacgtgg aggtgcgcac ggccaggaca aagccgagag aggagcagtt caacagcacc    900
ttccgcgtgg tcagcgccct gcccatccag caccaagact ggactggagg aaaggagttc    960
aagtgcaagg tccacaacga aggcctcccg gcccccatcg tgaggaccat ctccaggacc   1020
aaagggcagg cccgggagcc gcaggtgtac gtcctggccc accccaggaa gagctcagc    1080 aaaagcacgc tcagcgtcac ctgcctggtc accggcttct acccagacta catcgccgtg   1140
gagtggcaga aaaatgggca gcctgagtcg gaggacaagt acggcacgac acatcccag    1200 ctggacgccg acggctccta cttcctgtac agcaggctca gggtggacaa gaacagctgg   1260
caagaaggag acacctacgc gtgtgtggtg atgcacgagg ctctgcacaa ccactacaca   1320
cagaagtcga tctctaagcc tccgggtaaa                                    1350
```

<210> SEQ ID NO 12
<211> LENGTH: 217
<212> TYPE: PRT
<213> ORGANISM: Artificial Sequence
<220> FEATURE:
<223> OTHER INFORMATION: light chain of antibody S-23.4.66

<400> SEQUENCE: 12

```
Gln Ala Val Leu Thr Gln Pro Ser Ser Val Ser Arg Ser Pro Gly Gln
1               5                   10                  15

Ser Val Ser Ile Thr Cys Ser Gly Ser Ser Ser Asn Val Gly Tyr Gly
            20                  25                  30

Asn Tyr Val Gly Trp Phe Gln Gln Val Pro Gly Ser Ala Pro Lys Leu
        35                  40                  45

Leu Ile Tyr Ser Ala Thr Ser Arg Ala Ser Gly Val Pro Asp Arg Phe
    50                  55                  60

Ser Gly Ser Arg Ala Gly Asn Thr Ala Thr Leu Thr Ile Thr Ser Leu
65                  70                  75                  80

Gln Ala Glu Asp Glu Ala Asp Tyr Tyr Cys Val Ser Tyr Asp Ser Ser
                85                  90                  95

Ser Lys Phe Gly Val Phe Gly Ser Gly Thr Arg Leu Thr Val Leu Gly
            100                 105                 110

Gln Pro Lys Ser Ala Pro Ser Val Thr Leu Phe Pro Pro Ser Thr Glu
        115                 120                 125

Glu Leu Ser Thr Asn Lys Ala Thr Val Val Cys Leu Ile Asn Asp Phe
    130                 135                 140

Tyr Pro Gly Ser Val Asn Val Val Trp Lys Ala Asp Gly Ser Thr Ile
145                 150                 155                 160

Asn Gln Asn Val Lys Thr Thr Gln Ala Ser Lys Gln Ser Asn Ser Lys
                165                 170                 175

Tyr Ala Ala Ser Ser Tyr Leu Thr Leu Thr Gly Ser Glu Trp Lys Ser
            180                 185                 190

Lys Ser Ser Tyr Thr Cys Glu Val Thr His Glu Gly Ser Thr Val Thr
        195                 200                 205

Lys Thr Val Lys Pro Ser Glu Cys Ser
    210                 215
```

<210> SEQ ID NO 13
<211> LENGTH: 455
<212> TYPE: PRT
<213> ORGANISM: Artificial Sequence
<220> FEATURE:
<223> OTHER INFORMATION: heavy chain of antibody S-23.4.66

```
<400> SEQUENCE: 13

Gln Val Arg Met Gln Glu Leu Gly Pro Ser Leu Val Lys Pro Ser Gln
 1               5                  10                  15

Thr Leu Ser Leu Thr Cys Thr Val Ser Gly Phe Ser Val Thr Asn Ser
            20                  25                  30

Gly Val Gly Trp Val Arg Gln Ala Pro Gly Lys Ala Leu Glu Trp Leu
        35                  40                  45

Gly Ile Ile Asn Asn Asp Gly Val Ala Gly Tyr Asn Pro Ala Leu Lys
    50                  55                  60

Thr Arg Leu Ser Ile Thr Arg Asp Thr Ser Lys Asn Gln Val Ser Leu
65                  70                  75                  80

Ser Leu Ser Ser Val Thr Thr Glu Asp Thr Ala Val Tyr Tyr Cys Gly
                85                  90                  95

Thr Arg Asp Leu Pro Ser Asp Val Arg Tyr Gly Asn Met Tyr Ile Asn
            100                 105                 110

Tyr Trp Gly Pro Gly Arg Met Val Thr Val Ser Ser Ala Ser Thr Thr
        115                 120                 125

Pro Pro Lys Val Tyr Pro Leu Thr Ser Cys Cys Gly Asp Thr Ser Ser
    130                 135                 140

Ser Ile Val Thr Leu Gly Cys Leu Val Ser Ser Tyr Met Pro Glu Pro
145                 150                 155                 160

Val Thr Val Thr Trp Asn Ser Gly Ala Leu Thr Ser Gly Val His Thr
                165                 170                 175

Phe Pro Ala Ile Leu Gln Ser Ser Gly Leu Tyr Ser Leu Ser Ser Val
            180                 185                 190

Val Thr Val Pro Ala Ser Thr Ser Gly Ala Gln Thr Phe Ile Cys Asn
        195                 200                 205

Val Ala His Pro Ala Ser Ser Thr Lys Val Asp Lys Arg Val Glu Pro
    210                 215                 220

Gly Cys Pro Asp Pro Cys Lys His Cys Arg Cys Pro Pro Glu Leu
225                 230                 235                 240

Pro Gly Gly Pro Ser Val Phe Ile Phe Pro Pro Lys Pro Lys Asp Thr
            245                 250                 255

Leu Thr Ile Ser Gly Thr Pro Glu Val Thr Cys Val Val Val Asp Val
        260                 265                 270

Gly Gln Asp Asp Pro Glu Val Gln Phe Ser Trp Phe Val Asp Asn Val
    275                 280                 285

Glu Val Arg Thr Ala Arg Thr Lys Pro Arg Glu Glu Gln Phe Asn Ser
290                 295                 300

Thr Phe Arg Val Val Ser Ala Leu Pro Ile Gln His Gln Asp Trp Thr
305                 310                 315                 320

Gly Gly Lys Glu Phe Lys Cys Lys Val His Asn Glu Gly Leu Pro Ala
                325                 330                 335

Pro Ile Val Arg Thr Ile Ser Arg Thr Lys Gly Gln Ala Arg Glu Pro
            340                 345                 350

Gln Val Tyr Val Leu Ala Pro Pro Gln Glu Glu Leu Ser Lys Ser Thr
        355                 360                 365

Leu Ser Val Thr Cys Leu Val Thr Gly Phe Tyr Pro Asp Tyr Ile Ala
    370                 375                 380

Val Glu Trp Gln Lys Asn Gly Gln Pro Glu Ser Glu Asp Lys Tyr Gly
385                 390                 395                 400

Thr Thr Thr Ser Gln Leu Asp Ala Asp Gly Ser Tyr Phe Leu Tyr Ser
                405                 410                 415
```

```
Arg Leu Arg Val Asp Lys Asn Ser Trp Gln Glu Gly Asp Thr Tyr Ala
            420                 425                 430

Cys Val Val Met His Glu Ala Leu His Asn His Tyr Thr Gln Lys Ser
        435                 440                 445

Ile Ser Lys Pro Pro Gly Lys
    450             455

<210> SEQ ID NO 14
<211> LENGTH: 651
<212> TYPE: DNA
<213> ORGANISM: Artificial Sequence
<220> FEATURE:
<223> OTHER INFORMATION: nucleic acid sequence for light chain of
      antibody S-23.4.66

<400> SEQUENCE: 14
caggctgtgc tgactcagcc gtcctccgtg tccaggtccc cgggccagag tgtctccatc      60
acctgctctg gaagcagcag caacgttgga tatggtaatt atgtgggctg gttccaacaa     120
gtcccaggat cagcccccaa actcctcatc tatagtgcga ccagtcgagc ctcggggggtc     180 cccgaccgat tctccggctc cagggctggc aacacagcga ccctgaccat cacttcgctc     240
caggctgagg acgaggccga ttattattgt gtatcttatg acagtagtag caaatttggt     300
gttttcggca gcgggaccag gctgaccgtc ctgggtcagc ccaagtccgc accctcggtc     360
accctgttcc cgccttccac cgaggagctc agtaccaaca ggccaccgt ggtgtgtctc      420 atcaacgact ctacccgggg tagcgtgaac gtggtctgga aggcagatgg cagcaccatc     480
aatcagaacg tgaagaccac ccaggcctcc aaacagagca acagcaagta cgcggccagc     540
agctacctga ccctgacggg cagcgagtgg aagtctaaga gcagttacac ctgcgaggtc     600
acgcacgagg ggagcaccgt gacgaagaca gtgaagccct cagagtgttc t              651

<210> SEQ ID NO 15
<211> LENGTH: 1365
<212> TYPE: DNA
<213> ORGANISM: Artificial Sequence
<220> FEATURE:
<223> OTHER INFORMATION: nucleic acid sequence for heavy chain of
      antibody S-23.4.66

<400> SEQUENCE: 15
caggtgcgga tgcaggagtt gggacccagc ctggtgaagc cctcacagac cctctccctc      60
acgtgcacgg tctctggatt ctcagtaacc aacagtggtg taggctgggt ccgccaggct     120
ccaggaaagg ccctggagtg gcttggtatt ataaataatg atggagtcgc aggctataac     180
ccagccctta agacccggct cagcatcacc agggacacct caagaaccca gtctccctg      240 tcattgagca gcgtgacaac tgaggacacg gccgtgtact actgtggaac acgagatttg     300
cccagtgatg ttcgttatgg gaacatgtat atcaactact ggggcccagg acgaatggtc     360
accgtctcct cagcctccac cacacccccg aaagtctacc ctctgacttc ttgctgcggg     420
gacacgtcca gctccatcgt gaccctgggc tgcctggtct ccagctatat gcccgagccg     480
gtgaccgtga cctggaactc tggtgccctg accagcggcg tgcacacctt ccggccatc     540 ctgcagtcct ccgggctcta ctctctcagc agcgtggtga ccgtgccggc cagcacctca     600
ggagcccaga ccttcatctg caacgtagcc caccggcca gcagcaccaa ggtggacaag     660
cgtgttgagc ccggatgccc ggaccatgc aaacattgcc gatgcccacc cctgagctc      720 cccggaggac cgtctgtctt catcttccca ccgaaaccca aggacaccct tacaatctct     780
```

```
ggaacgcccg aggtcacgtg tgtggtggtg gacgtgggcc aggatgaccc cgaggtgcag    840
ttctcctggt tcgtggacaa cgtggaggtg cgcacggcca ggacaaagcc gagagaggag    900
cagttcaaca gcaccttccg cgtggtcagc gccctgccca tccagcacca agactggact    960
ggaggaaagg agttcaagtg caaggtccac aacgaaggcc tcccggcccc catcgtgagg   1020
accatctcca ggaccaaagg gcaggcccgg gagccgcagg tgtacgtcct ggccccaccc   1080
caggaagagc tcagcaaaag cacgctcagc gtcacctgcc tggtcaccgg cttctaccca   1140
gactacatcg ccgtggagtg gcagaaaaat gggcagcctg agtcggagga caagtacggc   1200
acgaccacat cccagctgga cgccgacggc tcctacttcc tgtacagcag gctcagggtg   1260
gacaagaaca gctggcaaga aggagacacc tacgcgtgtg tggtgatgca cgaggctctg   1320
cacaaccact acacacagaa gtcgatctct aagcctccgg gtaaa                   1365
```

<210> SEQ ID NO 16
<211> LENGTH: 6
<212> TYPE: PRT
<213> ORGANISM: Artificial Sequence
<220> FEATURE:
<223> OTHER INFORMATION: CDR1, light chain, antibody S-22.2.195

<400> SEQUENCE: 16

Leu Leu Asp Asp Ala Tyr
1               5

<210> SEQ ID NO 17
<211> LENGTH: 10
<212> TYPE: PRT
<213> ORGANISM: Artificial Sequence
<220> FEATURE:
<223> OTHER INFORMATION: CDR3, light chain, antibody S-22.2.195

<400> SEQUENCE: 17

Leu Ser Val Asp Ser Ser Glu Tyr Ser Val
1               5                   10

<210> SEQ ID NO 18
<211> LENGTH: 8
<212> TYPE: PRT
<213> ORGANISM: Artificial Sequence
<220> FEATURE:
<223> OTHER INFORMATION: CDR1, heavy chain, antibody S-22.2.195

<400> SEQUENCE: 18

Gly Phe Ser Leu Ile Gly Glu Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: CDR2, heavy chain, antibody S-22.2.195

<400> SEQUENCE: 19

Met Ala Ser Gly Gly Thr Ile
1               5

<210> SEQ ID NO 20
<211> LENGTH: 13
<212> TYPE: PRT
<213> ORGANISM: Artificial Sequence
<220> FEATURE:

<223> OTHER INFORMATION: CDR3, heavy chain, antibody S-22.2.195

<400> SEQUENCE: 20

Val Arg Ser Ser Val Ser Pro Gly Asp Asp Arg Asp Val
1               5                   10

<210> SEQ ID NO 21
<211> LENGTH: 9
<212> TYPE: PRT
<213> ORGANISM: Artificial Sequence
<220> FEATURE:
<223> OTHER INFORMATION: CDR1, light chain, antibody S-23.4.66

<400> SEQUENCE: 21

Ser Ser Asn Val Gly Tyr Gly Asn Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: CDR3, light chain, antibody S-23.4.66

<400> SEQUENCE: 22

Val Ser Tyr Asp Ser Ser Ser Lys Phe Gly Val
1               5                   10

<210> SEQ ID NO 23
<211> LENGTH: 8
<212> TYPE: PRT
<213> ORGANISM: Artificial Sequence
<220> FEATURE:
<223> OTHER INFORMATION: CDR1, heavy chain, antibody S-23.4.66

<400> SEQUENCE: 23

Gly Phe Ser Val Thr Asn Ser Gly
1               5

<210> SEQ ID NO 24
<211> LENGTH: 7
<212> TYPE: PRT
<213> ORGANISM: Artificial Sequence
<220> FEATURE:
<223> OTHER INFORMATION: CDR2, heavy chain, antibody S-23.4.66

<400> SEQUENCE: 24

Ile Asn Asn Asp Gly Val Ala
1               5

<210> SEQ ID NO 25
<211> LENGTH: 18
<212> TYPE: PRT
<213> ORGANISM: Artificial Sequence
<220> FEATURE:
<223> OTHER INFORMATION: CDR3, heavy chain, antibody S-23.4.66

<400> SEQUENCE: 25

Gly Thr Arg Asp Leu Pro Ser Asp Val Arg Tyr Gly Asn Met Tyr Ile
1               5                   10                  15

Asn Tyr

<210> SEQ ID NO 26
<211> LENGTH: 92
<212> TYPE: PRT
<213> ORGANISM: Artificial Sequence
<220> FEATURE:
<223> OTHER INFORMATION: NT-proBNP with R46H mutation with additional
      sequences such as His tag

<400> SEQUENCE: 26

```
Met Arg Gly Ser His Pro Leu Gly Ser Pro Gly Ser Ala Ser Asp Leu
1               5                   10                  15

Glu Thr Ser Gly Leu Gln Glu Gln Arg Asn His Leu Gln Gly Lys Leu
            20                  25                  30

Ser Glu Leu Gln Val Glu Gln Thr Ser Leu Glu Pro Leu Gln Glu Ser
        35                  40                  45

Pro Arg Pro Thr Gly Val Trp Lys Ser Arg Glu Val Ala Thr Glu Gly
    50                  55                  60

Ile Arg Gly His Arg Lys Met Val Leu Tyr Thr Leu Arg Ala Pro Arg
65                  70                  75                  80

Gly Gly Gly Ser His His His His His His His
                85                  90
```

<210> SEQ ID NO 27
<211> LENGTH: 88
<212> TYPE: PRT
<213> ORGANISM: Artificial Sequence
<220> FEATURE:
<223> OTHER INFORMATION: NT-proBNP with R46H mutation with additional
      sequences such as His tag

<400> SEQUENCE: 27

```
His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Gln Thr Ser Leu Glu Pro Leu Gln Glu Ser Pro His Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg Gly Gly Gly Ser
65                  70                  75                  80

His His His His His His His
                85
```

<210> SEQ ID NO 28
<211> LENGTH: 92
<212> TYPE: PRT
<213> ORGANISM: Artificial Sequence
<220> FEATURE:
<223> OTHER INFORMATION: NT-proBNP with E43D mutation with additional
      sequences such as His tag

<400> SEQUENCE: 28

```
Met Arg Gly Ser His Pro Leu Gly Ser Pro Gly Ser Ala Ser Asp Leu
1               5                   10                  15

Glu Thr Ser Gly Leu Gln Glu Gln Arg Asn His Leu Gln Gly Lys Leu
            20                  25                  30

Ser Glu Leu Gln Val Glu Gln Thr Ser Leu Glu Pro Leu Gln Asp Ser
        35                  40                  45

Pro Arg Pro Thr Gly Val Trp Lys Ser Arg Glu Val Ala Thr Glu Gly
    50                  55                  60

Ile Arg Gly His Arg Lys Met Val Leu Tyr Thr Leu Arg Ala Pro Arg
65                  70                  75                  80
```

```
Gly Gly Gly Ser His His His His His His His
            85                  90

<210> SEQ ID NO 29
<211> LENGTH: 4
<212> TYPE: PRT
<213> ORGANISM: Artificial Sequence
<220> FEATURE:
<223> OTHER INFORMATION: N-terminal sequence in fusion proteins

<400> SEQUENCE: 29

Met Arg Gly Ser
1

<210> SEQ ID NO 30
<211> LENGTH: 4
<212> TYPE: PRT
<213> ORGANISM: Artificial Sequence
<220> FEATURE:
<223> OTHER INFORMATION: C-terminal sequence in fusion proteins

<400> SEQUENCE: 30

Gly Gly Gly Ser
1
```

ANTIBODIES RECOGNIZING GENETIC VARIANTS OF NT-PROBNP

CROSS-REFERENCE TO RELATED APPLICATIONS

This application is a continuation of International Application No. PCT/EP2018/053474 filed Feb. 13, 2018, which claims priority to European Application No. 17155810.9 filed Feb. 13, 2017, the disclosures of which are hereby incorporated by reference in their entirety.

SUMMARY OF THE INVENTION

The present invention relates to i) an antibody that specifically binds a mutated NT-proBNP comprising a mutation substituting arginine at position 46 with histidine, and ii) an antibody that specifically binds a mutated NT-proBNP comprising a mutation substituting glutamic acid at position 43 with aspartic acid. Moreover, the present invention relates to a mutated NT-proBNP. Further envisaged by the present invention are kits comprising the antibody of the present invention, or the mutated NT-proBNP of the present invention. The present invention also concerns a method for diagnosing heart failure.

Heart failure (HF) is among the leading causes of morbidity and mortality in many countries worldwide. Measurement of natriuretic peptide markers, such as B-type natriuretic peptide (BNP), or its amino-terminal fragment N-terminal proBNP (NT-proBNP), has emerged as an important tool for the diagnosis and risk stratification of patients with HF.

Brain natriuretic peptide (BNP) is a 32-amino acid polypeptide. BNP is synthesized as a 134-amino acid pre-prohormone ("pre-proBNP"). Removal of the N-terminal signal peptide which has a length of 26 amino acids generates the prohormone ("proBNP", 108 aa long). The prohormone is subsequently cleaved into NT-proBNP (N-terminal of the prohormone brain natriuretic peptide, 76 aa long) and the biologically active brain natriuretic peptide (BNP). NT-proBNP and BNP are produced in equimolar amounts. Several studies showed that assays for BNP and NT-proBNP can be reliably used for the diagnosis of heart failure (see e.g. Prontera et al., Clinica Chimica Acta 400 (2009) 70-73).

BNP is metabolized in the blood. It has a short half life due to a rapid degradation rate both in vivo and in vitro. NT-proBNP circulates in the blood as an intact molecule and as such is eliminated renally. It has a higher half life and is more stable in vitro than the active peptide BNP. Preanalytics are thus more robust with NT-proBNP allowing easy transportation of the sample to a central laboratory (Mueller 2004, Clin Chem Lab Med 42: 942-4). Blood samples can be stored at room temperature for several days or may be mailed or shipped without recovery loss. In contrast, storage of BNP for 48 hours at room temperature or at 4° Celsius leads to a concentration loss of at least 20% (Mueller loc.cit.; Wu 2004, Clin Chem 50: 867-73).

Due to the advantages of NT-proBNP, the biologically inactive peptide NT-proBNP is currently the preferred marker for the diagnosis of heart failure. The marker is routinely used in laboratory testing, but also in the point-of-care setting.

All NT-proBNP assays currently on the market are sandwich-immunoassays using a capture and a signal antibody. Some of the NT-proBNP assays currently on the market contain antibodies which bind to an epitope comprising amino acids 42 to 46 of NT-proBNP (see Saenger et al, Clinical Chemistry 63:1 351-358 (2017), e.g. supplemental table 2, or Clerico et al., Crit Rev Clin Lab Sci, 2015; 52(2): 56-69).

In the studies underlying the present invention, a point mutation was identified in the amino acid sequence of NT-proBNP (Arg46His, R46H). This point mutation is within the epitope of the signal antibodies of various NT-proBNP assays. The point mutation can be found in Ensembl-database (Yates et al. Ensembl 2016, Nucleic Acids Res. 2016 44 Database Issue:D710-6, release 87, December 2016, dbSNP Cluster ID: rs61761991. Search of databases revealed a second point mutation Glu43Asp (E43D) within amino acids 42 to 46 of NT-proBNP (dbSNP Cluster ID: rs74613227).

It is an object of the present invention to provide means and methods for diagnosing heart failure in subjects having mutations in the amino acid sequence of NT-proBNP. The technical problem is solved by the embodiments characterized in the claims and herein below.

Accordingly, the present invention relates to an antibody that specifically binds a mutated NT-proBNP comprising a mutation substituting arginine at position 46 with histidine. Further, the present invention relates to an antibody that specifically binds a mutated NT-proBNP comprising a mutation substituting glutamic acid at position 43 with aspartic acid.

The term "NT-proBNP" (N-terminal fragment of pro-brain natriuretic peptide) is well known in the art. As used herein, the term relates to the 76 amino acid N-terminal fragment of pro brain natriuretic peptide (proBNP) which is a secreted protein which, after cleavage, functions as a cardiac hormone. Preferably, NT-proBNP is human NT-proBNP. Thus, said mutated NT-proBNP shall be mutated human NT-proBNP.

The sequence of the wild-type human NT-proBNP (herein also referred to as "unmutated" NT-proBNP) is well known in the art and has been described already in detail in the prior art, e.g., WO 02/089657, WO 02/083913, Bonow 1996, New Insights into the cardiac natriuretic peptides. Circulation 93: 1946-1950. Preferably, the wild-type NT-proBNP has an amino acid sequence as shown in SEQ ID NO: 3.

The antibodies of the present invention shall specifically bind to a mutated NT-proBNP. Thus, the NT-proBNP specifically bound by the antibodies of the present invention shall comprise a mutation as compared to the wild-type NT-proBNP.

BRIEF DESCRIPTION OF THE FIGURES

FIGS. 1A and 1B: Concentration dependent antibody kinetics for antibody S-23.4.66 and for antibody rS-22.2.195 (see Example 3).

FIGS. 2A and 2B: Antibody sandwich experiments with recombinant proBNP and M-18.4.34-IgG as primary antibody and S-23.4.66-IgG or rS-22.2.195-IgG as secondary antibodies. M-18.4.34-IgG was applied as homologous secondary antibody control (see Example 4).

DETAILED DESCRIPTION OF THE INVENTION

Figure 1A:
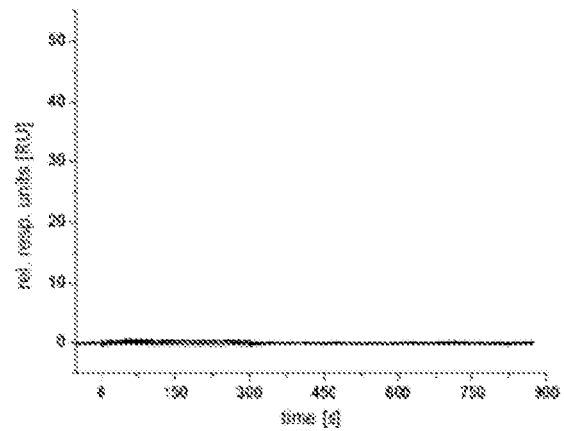
In FIGS. 1A and 1B and 2A and 2B and in the following Examples section, reference is made to the mutations R72H and E69D in NT-proBNP. As described herein elsewhere, the R72H mutation is the same mutation as the R46H mutation, and the E69D mutation is the same mutation as the E46D mutation.
Figure 1A:
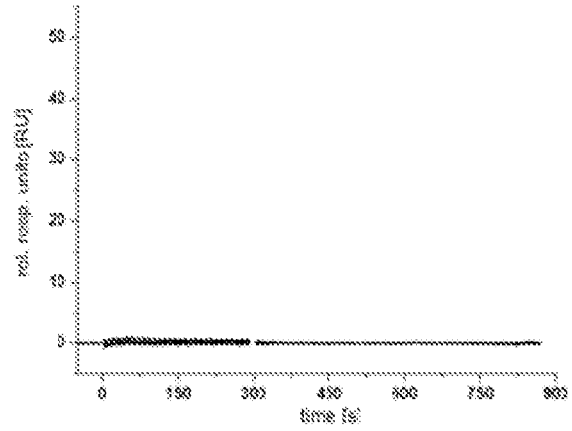
Figure 1A:
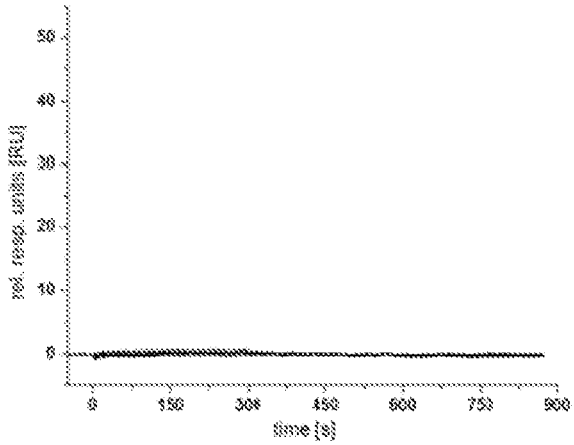
Figure 1A:
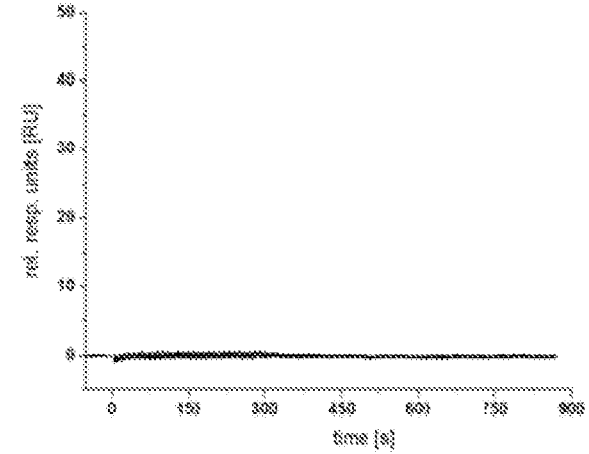

In an embodiment, the antibody of the present invention shall specifically bind to mutated NT-proBNP comprising a mutation substituting arginine at position 46 with histidine. Thus, the arginine at position 46 of the wild-type NT-proBNP shall be substituted with histidine (in other words, this mutated NT-proBNP comprises histidine at position 46). This mutation is herein also referred to as the "Arg46His", or "R46H" mutation.

In another embodiment, the antibody of the present invention specifically binds to mutated NT-proBNP comprising a mutation substituting glutamic acid at position 43 with aspartic acid. Thus, the glutamic acid at position 43 of the wild-type NT-proBNP shall be substituted with aspartic acid (in other words, this mutated NT-proBNP comprises aspartic acid at position 43). This mutation is herein also referred to as the "Glu43Asp", or "E43D" mutation.

The positions of the mutations given herein are the amino acid positions in the sequence of NT-proBNP, in particular in the wild-type NT-proBNP having a sequence as shown in SEQ ID NO: 3. Thus, the R46H mutation is at position 46 of NT-proBNP. In the longer precursor polypeptide, preproBNP, the corresponding mutation is at position 72. Therefore, the R46H mutation is herein, e.g. in the Examples section, also referred to as R72H mutation, and the E43D mutation as E69D mutation.

The mutations referred to above are substitutions. It is to be understood that the mutations/substitutions are mutations/substitutions compared to the wild-type NT-proBNP, in particular as compared to the wild-type NT-proBNP having a sequence as shown in SEQ ID NO: 3. For example, the wild-type human NT-proBNP comprises an arginine residue at position 46, whereas the mutated NT-proBNP comprising a mutation substituting arginine at position 46 with histidine comprises a histidine residue at this position.

One or more further mutations may be present in the mutated NT-proBNP. However, these one or more mutations shall not be located in the epitope specifically bound by the antibody of the present invention.

In an embodiment of the present invention, the mutated NT-proBNP comprising a mutation substituting arginine at position 46 with histidine comprises an amino acid sequence as shown in SEQ ID NO: 1. The sequence is also shown in Table A. The histidine residue at position 46 is indicated in bold.

In an embodiment, the mutated NT-proBNP comprising a mutation substituting glutamic acid at position 43 with aspartic acid comprises an amino acid sequence as shown in SEQ ID NO: 2. The sequence is also shown in Table A. The aspartic acid residue at position 43 is indicated in bold.

The term "antibody" is known in the art. As used herein, the term refers to any immunoglobulin (Ig) molecule comprised of four polypeptide chains, two heavy (H) chains and two light (L) chains. As used herein, the term "antibody" also includes an antigen-binding fragment of the antibody. The term "antigen-binding fragment" is explained elsewhere herein. The definition applies accordingly.

The antibody in accordance with the present invention can be a polyclonal or monoclonal antibody. In a preferred embodiment, the antibody is a monoclonal antibody. The term "monoclonal antibody" is well known in the art. As used herein, the term preferably refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. A monoclonal antibody of the present invention can be made by the well-known hybridoma method described by Kohler and Milstein, Nature, 256:495 (1975), or can be made by recombinant DNA methods.

In a preferred embodiment of the present invention, the antibody is prepared by applying a mutated NT-proBNP or fragment of the present invention (as described elsewhere herein in more detail) to a mammal, preferably a mouse, more preferably to a sheep. In particular, it is envisaged that NT-proBNP or fragment thereof comprises (and thus is operably linked) to a carrier protein (for a definition of the term "carrier protein" see elsewhere herein). Depending on the host species, various adjuvants can be used to increase the immunological response. Such adjuvants encompass, preferably, Freund's adjuvant, mineral gels, e.g., aluminum hydroxide, and surface active substances, e.g., lysolecithin, pluronic polyols, polyanions, peptides, oil emulsions, keyhole limpet hemocyanin, and dinitrophenol. Monoclonal antibodies according to the invention can be subsequently prepared using the well known hybridoma technique. Further details on the preparation of an antibody of the invention are described in the accompanying Examples below.

A preferred antibody of the present invention is an IgG antibody.

In an embodiment, the antibody of the present invention is an isolated antibody. Thus, the antibody shall be an antibody which has been purified. Purification of an antibody can be achieved by methods well known in the art such as Size Exclusion Chromatography (SEC). Accordingly, the antibody shall have been isolated from the cells in which the antibody was produced. In some embodiments, an isolated antibody is purified to greater than 70% by weight of antibody as determined by, for example, the Lowry method, and in some embodiments, to greater than 80%, 90%, 95%, 96%, 97%, 98% or 99% by weight. In one preferred embodiment the isolated antibody according to the present invention is purified to greater than 90% purity as determined by SDS-PAGE under reducing conditions using Coomassie blue staining for protein detection.

Preferably, the monoclonal antibody as described herein is selected from a group consisting of a sheep monoclonal antibody, a mouse monoclonal antibody, a rabbit monoclonal antibody, a goat monoclonal antibody, a horse monoclonal antibody, a chicken monoclonal antibody. More preferably, the monoclonal antibody is a mouse monoclonal antibody. Most preferably, the monoclonal antibody is a sheep antibody.

The antibody of the present invention can be used in a sandwich assay as capture or detection (signal) antibody in combination with at least one other antibody binding to a different, i.e. second NT-proBNP epitope. Preferably, the second antibody derived from a species which differs from the species from which the antibody of the present invention has been obtained. For example, if the antibody of the present invention is a sheep antibody, the second antibody could be a mouse antibody.

The signal and the capture antibody can be used in sandwich assays. Sandwich assays are among the most useful and commonly used assays encompassing a number of variations of the sandwich assay technique. For example, in a typical assay, an unlabeled (capture) binding agent is immobilized or can be immobilized on a solid substrate, and the sample to be tested is brought into contact with the capture binding agent. After a suitable period of incubation, for a period of time sufficient to allow formation of a binding agent-biomarker complex, a second (detection) binding agent labeled with a reporter molecule capable of producing a detectable signal is then added and incubated, allowing time sufficient for the formation of another complex of binding agent-biomarker-labeled binding agent. Any unreacted material may be washed away, and the presence of the biomarker is determined by observation of a signal produced by the reporter molecule bound to the detection binding agent. The results may either be qualitative, by simple observation of a visible signal, or may be quantitated by comparison with a control sample containing e.g. known amounts of the mutated NT-proBNP (as standard or calibrator as described elsewhere herein).

The incubation steps of a typical sandwich assay can be varied as required and appropriate. Such variations include for example simultaneous incubations, in which two or more of binding agent and biomarker are co-incubated. For example, both, the sample to be analyzed and a labeled binding agent are added simultaneously to an immobilized capture binding agent. It is also possible to first incubate the sample to be analyzed and a labeled binding agent and to thereafter add an antibody bound to a solid phase or capable of binding to a solid phase.

The formed complex between a specific binding agent and the biomarker shall be proportional to the amount of the biomarker present in the sample. It will be understood that the specificity and/or sensitivity of the binding agent to be applied defines the degree of proportion of at least one marker comprised in the sample which is capable of being specifically bound. Further details on how the measurement can be carried out are also found elsewhere herein. The amount of formed complex shall be transformed into an amount of the biomarker reflecting the amount indeed present in the sample.

An antibody as set forth herein may be comprised by a test strip.

The antibody (or antigen binding fragment thereof) of the present invention shall be capable of specifically binding a mutated NT-proBNP (N-terminal fragment of pro-brain natriuretic peptide). Thus, the antibody of the present invention (or antigen-binding fragment thereof) shall be capable of specifically binding to an epitope comprised by the mutated NT-proBNP. The term "epitope" is well known in the art. As used herein, the term preferably refers to the portion of the mutated NT-proBNP capable of being specifically bound by the antibody of the present invention. However, an epitope in accordance with the present invention can also be formed by a certain three-dimensional structure and such structural epitopes are also envisaged herein. In an embodiment, the epitope has a length of at least five, but not more than 50 amino acids, in particular not more than 20 amino acids.

It is to be understood that the epitope shall comprise the mutation as referred to herein, i.e. the mutated amino acid residue. Thus, the antibody of the present invention shall bind to an epitope in the mutated NT-proBNP which comprises the mutation (and thus the histidine residue at position 46 of NT-proBNP or the aspartic acid residue at position 43 of NT-proBNP).

The antibody as described herein, or antigen binding fragment thereof, shall specifically bind to the corresponding antigen (e.g. the mutated NT-proBNP, or fragment thereof as defined elsewhere herein). An antibody that "binds" or "specifically binds" to an antigen, thus, is intended to refer to an antibody (or antigen-binding fragment thereof) that specifically binds to the antigen. The expression "specific binding" or "specifically binding" well understood and is used to indicate that an antibody (or antigen binding fragment thereof) does not significantly bind to other biomolecules. In particular, an antibody that specifically binds to a mutated NT-proBNP as set forth herein (or fragment thereof) preferably does not bind to wild-type NT-proBNP (and thus to NT-proBNP not comprising a mutation substituting arginine at position 46 with histidine and/or a mutation substituting glutamic acid at position 43 with aspartic acid). The expression that "an antibody does not bind wild-type NT-proBNP" or that "a fragment of the antibody does not bind wild-type-NT-proBNP", means that the antibody (or fragment thereof) does not significantly bind wild-type NT-proBNP. For example, as described herein below, it is envisaged that the $K_D$ of the antibody of the present invention (or of the fragment thereof) to wild-type NT-proBNP is at least hundredfold lower than its $K_D$ to the mutated NT-proBNP as referred to herein.

Accordingly, the level of binding to wild-type NT-proBNP results in a negligible binding affinity by means of ELISA or an affinity determination e.g. using a Biacore T200 instrument. As shown in the Examples, kinetic measurements do not show any determinable association rate constant ka (1 Ms) of such antibody versus wild-type NT-proBNP, even at high analyte concentrations.

$K_D$ is the dissociation constant which can be determined with a binding assay, such as surface plasmon resonance techniques (BIAcore®, GE-Healthcare Uppsala, Sweden). As described in the Examples section, two monoclonal antibodies, named S-22.2.195 and S-23.4.66, were generated and tested in the studies underlying the present invention. Antibody S-22.2.195 binds to NT-proBNP with the R46H mutation. Antibody S-23.4.66 binds to NT-proBNP with the E43D mutation. The $K_D$, $k_a$ and $k_d$ values of these antibodies for wild-type NT-proBNP, NT-proBNP with the R46H mutation, and NT-proBNP with the E43D mutation were determined in Example 3 of the Examples section.

In particular, the antibody (or antigen binding fragment thereof) that specifically binds to mutated NT-proBNP R46H, as referred to herein, preferably has a $K_D$ value for the antigen (i.e. the NT-proBNP comprising a mutation substituting arginine at position 46 with histidine) of not more than 0.05 nM at 13° C., in particular of not more than 0.08 nM at 25° C. and/or not more than 0.15 nM at 37° C.

In particular, the antibody of the present invention (or antigen binding fragment thereof) that specifically binds to mutated NT-proBNP E43D, as referred to herein, preferably has a $K_D$ value for the antigen (NT-proBNP comprising a mutation substituting glutamic acid at position 43 with aspartic acid) of not more than 0.4 nM at 13° C., in particular of not more than 3 nM at 25° C. and/or not more than 20 nM at 37° C.

It is in particularly envisaged that the antibody (or antigen binding fragment) of the present invention specifically binds to its genuine antigen and does not show detectable off-target interactions as investigated by means of SPR (Surface Plasmon Resonance).

Preferably, the antibody of the present invention (or the antigen-binding fragment thereof) shows lower affinity interactions versus recognizing wild-type NT-proBNP (as compared to the interactions versus its antigen, i.e. the mutated NT-proBNP. More preferably, the affinity $K_D$ of said antibody or fragment thereof to wild-type NT-proBNP is at least hundredfold lower, in particular at least threehundredfold lower than its binding to the antigen (i.e. the mutated NT-proBNP).

Another means to describe the kinetic binding properties of an antibody to its antigen is the resolution of the dissociation constant into its kinetic rate contributions, as there are the association rate $k_a$ constant and the dissociation rate constant $k_d$. The association rate $k_a$ constant characterizes the velocity of the antibody/antigen complex formation and is time and concentration dependent.

Preferably the association rate constant of an antibody (or antigen binding fragment thereof) that specifically binds to mutated NT-proBNP R46H, as referred to herein, preferably has a $k_a$ value (for its antigen) of more than 4.0E+05 1/Ms at 13° C., in particular more than 7.5E+05 1/Ms at 25° C. and/or more than 1.0E+06 1/Ms at 37° C.

Preferably the association rate constant of an antibody (or antigen binding fragment thereof) that specifically binds to mutated NT-proBNP E43D, as referred to herein, preferably has a $k_a$ value of more than 6.0E+04 1/Ms at 13° C., in particular more than 5.5E+04 1/Ms at 25° C. and more than 1.0E+05 1/Ms at 37° C.

Antibodies specifically binding mutated NT-proBNP as referred to herein, preferably show at least 1.6-fold slower association rate constants versus wild-type NT-proBNP at 25° C.

The dissociation rate constant indicates the dissociation rate of an antibody from its antigen. Thus, the dissociation rate constant indicates the probability that the complex will fall apart in a unit of time. The lower the dissociation rate constant, the more tightly bound the antibody is to its antigen.

Preferably the dissociation rate constant of an antibody (or antigen binding fragment thereof) that specifically binds to mutated NT-proBNP R46H, as referred to herein, preferably has a $k_d$ value of less than 1.0E-05 1/s at 13° C., in particular less than 3E-05 1/s at 25° C. and less than 9E-05 1/s at 37° C.

Preferably the dissociation rate constant of an antibody (or antigen binding fragment thereof) that specifically binds to mutated NT-proBNP E43D as referred to herein, preferably has a $k_d$ value of less than 1.0E-05 1/s at 13° C., in particular less than 1.5E-04 1/s at 25° C. and/or less than 2.0E03 1/s at 37° C.

Antibodies specifically binding mutated NT-proBNP as referred to herein, preferably show at least hundredfold faster dissociation rate constants versus wild-type NT-proBNP at 25° C. (as compared to the dissociation rate constants versus the mutated NT-proBNP).

The kinetic rate constants are changing in a temperature gradient. The temperature-dependent binding kinetics at 13° C. and 37° C. can be used to characterize antibody antigen interactions. The quotient of the association rate velocities at $k_a$ 37° C. and $k_a$ 13° C. (Velocity Factor, US20140256915) is a means to characterize antibody interactions. If the quotient is below a value of 10, the antibody antigen binding is enthalpy dominated, whereas a velocity factor VF>10 increases the likelihood of an entropy-driven kinetic.

Preferably the quotient of an antibody (or antigen binding fragment thereof) that specifically binds to wild-type NT-proBNP or fragments or muteins thereof is below 10.

The antibodies of the present invention shall comprise at least one light chain, in particular two light chains, and at least one heavy chain, in particular two heavy chains.

In a preferred embodiment of the present invention, the antibody binds mutated NT-proBNP comprising a mutation substituting arginine at position 46 with histidine. Preferably, the light chain (in particular both light chains) of said antibody comprises (comprise) the amino acid sequence of SEQ ID NO: 4, and the heavy chain (in particular both heavy chains) of said antibody comprises (comprise) the amino acid sequence of SEQ ID NO: 5.

The light chain comprising the amino acid sequence as shown in SEQ ID NO: 4 is preferably encoded by a polynucleotide comprising a nucleic acid sequence as shown in SEQ ID NO: 10. The heavy chain comprising the amino acid sequence as shown in SEQ ID NO: 5 is preferably encoded by a polynucleotide comprising a nucleic acid sequence as shown in SEQ ID NO: 11.

In another preferred embodiment of the present invention, the antibody binds to mutated NT-proBNP comprising a mutation substituting glutamic acid at position 43 with aspartic acid. Preferably, the light chain (in particular both light chains) of said antibody comprises (comprise) the amino acid sequence of SEQ ID NO: 12, and the heavy chain (in particular both heavy chains) of said antibody comprises (comprise) the amino acid sequence of SEQ ID NO: 13.

The light chain comprising the amino acid sequence as shown in SEQ ID NO: 12 is preferably encoded by a polynucleotide comprising a nucleic acid sequence as shown in SEQ ID NO: 14. The heavy chain comprising the amino acid sequence as shown in SEQ ID NO: 13 is preferably encoded by a polynucleotide comprising a nucleic acid sequence as shown in SEQ ID NO: 15.

Antibodies comprising the above light chains and heavy chains were produced in the studies underlying the present invention:

The antibody S-22.2.195 specifically binds to NT-proBNP with the R46H mutation. This antibody comprises light chains having a sequence as shown in SEQ ID NO: 4, and heavy chains having a sequence as shown in SEQ ID NO: 5.

The antibody S-23.4.66 specifically binds to NT-proBNP with the E43D mutation. This antibody comprises light chains having a sequence as shown in SEQ ID NO: 12, and heavy chains having a sequence as shown in SEQ ID NO: 13.

The amino acid sequences of the heavy and the light chains of the produced antibodies are also shown in Table A.

Table A further shows the complementary determining regions (CDRs) which are primarily responsible for the binding affinity of the antibody. Each light chain and heavy chain has three CDRs '(CDR1, CDR2, and CDR3). Thus, each antibody has a total of six different CDRs.

The CDRs of the heavy and the light chain of the two antibodies generated in the studies of the present invention are indicated in bold in Table A below (in order from N-terminus to C-terminus). The CDRs were annotated in silico (Lefranc, M.-P., IMGT, the International ImMunoGeneTics Information System Cold Spring Harb Protoc. 2011 Jun. 1;2011(6)).

In a preferred embodiment, the antibody (or antigen binding fragment thereof) of the present invention comprises the six CDRs comprised by S-22.2.195 or the six CDRs comprised by S23.4.66 (preferably in the same order as in the light chain/heavy chain of the respective antibody).

Accordingly, it is envisaged that the antibody (or antigen-binding fragment thereof) comprises in the light chain (preferably in both light chains):

a CDR1 having the sequence LLDDAY (as shown in SEQ ID NO: 16)

a CDR2 having the sequence KDS, and a CDR3 having the sequence LSVDSSEYSV (as shown in SEQ ID NO: 17), and in the heavy chain (preferably in both heavy chains):
a CDR1 having the sequence GFSLIGEY (as shown in SEQ ID NO: 18),
a CDR2 having the sequence MASGGTI (as shown in SEQ ID NO: 19), and
a CDR3 having the sequence VRSSVSPGDDRDV (as shown in SEQ ID NO: 20).

The above antibody specifically binds to NT-proBNP with the R46H mutation. Thus, the antibody which specifically binds to NT-proBNP with the R46H mutation is characterized in that the light chain variable domain comprises a CDR1 having the sequence LLDDAY (SEQ ID NO: 16), a CDR2 having the sequence KDS, and a CDR3 having the sequence LSVDSSEYSV (SEQ ID NO: 17), and the heavy chain variable domain comprises a CDR1 having the sequence GFSLIGEY (SEQ ID NO: 18), a CDR2 having the sequence MASGGTI (SEQ ID NO: 19), and a CDR3 having the sequence VRSSVSPGDDRDV (SEQ ID NO: 20).

Further, it is envisaged that the antibody (or antigen-binding fragment thereof) of the present invention comprises
in the light chain (preferably in both light chains):
a CDR1 having the sequence SSNVGYGNY (as shown in SEQ ID NO: 21)
a CDR2 having the sequence SAT, and
a CDR3 having the sequence VSYDSSSKFGV (as shown in SEQ ID NO: 22),
and
in the heavy chain (preferably in both heavy chains):
a CDR1 having the sequence GFSVTNSG (as shown in SEQ ID NO: 23),
a CDR2 having the sequence INNDGVA (as shown in SEQ ID NO: 24), and
a CDR3 having the sequence GTRDLPSDVRYGNMYINY (as shown in SEQ ID NO: 25).

The above described antibody specifically binds to NT-proBNP with the E43D mutation. Thus, the antibody which specifically binds to NT-proBNP with the E43D mutation is characterized in that the light chain variable domain comprises a CDR1 having the sequence SSNVGYGNY (SEQ ID NO: 21) a CDR2 having the sequence SAT, and a CDR3 having the sequence VSYDSSSKFGV (SEQ ID NO: 22), and the heavy chain variable domain a CDR1 having the sequence GFSVTNSG (SEQ ID NO: 23), a CDR2 having the sequence INNDGVA (SEQ ID NO: 24), and a CDR3 having the sequence GTRDLPSDVRYGNMYINY (SEQ ID NO: 25).

The CDRs referred to above shall be comprised by the variable regions of the respective long chain or short chain, preferably, in the order as shown in Table A.

The present invention also relates to an antigen-binding fragment (herein also referred to as "antibody fragment") of the antibody of the present invention. As used herein, an antigen-binding fragment of an antibody shall be capable of specifically binding to the antigen (in particular to the mutated NT-proBNP as described above, i.e. the mutated NT-proBNP comprising a mutation substituting arginine at position 46 with histidine or the mutated NT-proBNP a mutation substituting glutamic acid at position 43 with aspartic acid). Thus, antigen binding fragments of antibodies are fragments retaining the ability of the (full-length) antibody to specifically bind to the antigen (e.g. the mutated NT-proBNP).

Antibody fragments preferably comprise a portion of a full length antibody, preferably the variable domain thereof, or at least the antigen binding site thereof. In an embodiment, the antigen-binding fragment is selected from the group consisting of a Fab fragment, a Fab' fragment, a Facb fragment, a F(ab')$_2$ fragment, a scFv fragment, and a Fv fragment. For example, the antigen-binding fragment is a F(ab')$_2$ fragment.

How to produce antigen-binding fragments is well known in the art. For example, the fragments can be produced by enzymatic cleavage of an antibody of the present invention. In addition, the fragments can be generated by synthetic or recombinant techniques. Fab fragments are preferably generated by papain digestion of an antibody, Fab' fragments by pepsin digestion and partial reduction, F(ab')$_2$ fragments by pepsin digestion), and facb fragments by plasmin digestion. Fv or scFv fragments are preferably produced by molecular biology techniques.

The antigen binding fragment of an antibody may also be a diabody, which are small antibody fragments with two antigen-binding sites. Diabodies preferably comprise a heavy chain variable domain connected to a light chain variable domain in the same polypeptide chain.

In an embodiment of the present invention, the antibody of the present invention or the antigen-binding fragment is used as signal antibody or signal fragment (herein also referred to as detection antibody or detection fragment). The term signal antibody or signal fragment refers to an antibody or fragment that is capable of being detected either directly or through a label amplified by a detection means. In an alternative embodiment of the present invention, the antibody of the present invention or the antigen-binding fragment is used as capture antibody or capture fragment.

In a preferred embodiment, the antibody of the present invention or the antigen-binding fragment is linked to a detectable label. A detectable label as described herein is preferably a label which is not naturally linked to an antibody or antigen-binding fragment thereof. Thus, the detectable label is preferably heterologous with respect to the antibody. Suitable labels are any labels detectable by an appropriate detection method. In an embodiment said detectable label is an enzyme, biotin, a radioactive label, a fluorescent label, a chemiluminescent label, an electrochemiluminescent label, a gold label, or a magnetic label. In a preferred embodiment, the label is an electrochemiluminescent label.

Enzymatic labels include e.g. horseradish peroxidase, alkaline phosphatase, beta-galactosidase, and luciferase. The substrates for these enzymes are well known in the art. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate). A suitable enzyme-substrate combination may result in a colored reaction product, fluorescence or chemoluminescence, which can be measured according to methods known in the art. Fluorescent labels, e.g., include 5-carboxyfluorescein, fluorescein isothiocyanate, rhodamine, tetramethylrhodamine, Cy2, Cy3, and Cy5, fluorescent proteins such as GFP (Green Fluorescent Protein), Texas Red and the Alexa dyes. Radioactive labels, e.g., include radioactive isotopes of iodide, cobalt, selenium, tritium, carbon, sulfur and phosphorous. A radioactive label can be detected by any method known and appropriate, e.g. a light-sensitive film or a phosphor imager. Magnetic labels e.g. include paramagnetic and superparamagnetic labels. Chemiluminescent labels of use may include luminol, isoluminol, an aromatic acridinium ester, an imidazole, an acridinium salt or an oxalate ester.

In particular, it is envisaged that the antibodies described herein comprise an electrochemiluminescent label (in particular the signal antibodies).

The most commonly used electrochemiluminescent compound is ruthenium. Thus, the electrochemiluminescent label preferably comprises ruthenium. In particular, the electrochemiluminescent label shall comprise a bipyridine-ruthenium (II) complex. Thus, it is in particular envisaged that the antibody is a ruthenylated antibody. How to ruthenylate an antibody is described e.g. in the Examples section.

The present invention also relates to a host cell producing the antibody of the present invention, or the antigen-binding fragment thereof. In a preferred embodiment, the host producing the antibody of the present invention is a hybridoma cell. Moreover, the host cell may be any kind of cellular system which can be engineered to generate the antibodies according to the current invention. For example, the host cell may be an animal cell, in particular a mammalian cell. In one embodiment HEK293 cells or CHO cells are used as host cells. In another embodiment, the host cell is a non-human animal or mammalian cell.

For example, the antibody S-23.4.66 that was generated in the studies underlying the present invention was produced by hybridoma. The antibody rS-22.2.195 was produced by hybridoma and by a pool of CHO cells in which the antibody was recombinantly expressed (Chinese Hamster Ovary cells). Subsequently, a stable CHO line was generated for large scale production of this antibody.

The host cell in accordance with the present invention shall be an isolated cell. Thus, the host cell shall be present in a cell culture, in other words outside from an organism.

The host cell preferably comprises at least one polynucleotide encoding for the light chain of the antibody of the present invention and at least one polynucleotide encoding the heavy chain of the antibody of the present invention. Said polynucleotides shall be operably linked to suitable promoters.

In accordance with the present invention, it is further envisaged to use the antibody that specifically binds a mutated NT-proBNP comprising a mutation substituting arginine at position 46 with histidine (or the antigen-binding fragment thereof) in combination with the antibody that specifically binds a mutated NT-proBNP comprising a mutation substituting glutamic acid at position 43 with aspartic acid (or antigen-binding fragment thereof). The combined use of these antibodies will allow the detection of NT-proBNP in subjects comprising the R46H mutation and in subjects comprising the E43D mutation.

Further, it is envisaged to use the R46H antibody (or antigen binding fragment thereof), or the E43D antibody (or antigen binding fragment thereof), or both the R46H and E43D antibodies (or antigen binding fragments thereof) in combination with an antibody that specifically binds to wild-type NT-proBNP (or an antigen-binding fragment thereof). As used herein, an "antibody that specifically binds to wild-type NT-proBNP" preferably specifically binds to a region of the wild-type NT-proBNP comprising amino acid residues 42 to 46 of the wild-type NT-proBNP. Accordingly, said antibody shall bind an epitope comprised within amino acids 42 to 46 of the wild-type NT-proBNP. The epitope of this antibody thus shall not comprise the E43D and R46H mutation. Preferably the antibody that specifically binds to wild-type NT-proBNP does not significantly bind the mutated NT-proBNP having the E43D or R46H mutation.

Thus, the present invention also relates to a kit or composition comprising a) i) an antibody that specifically binds a mutated NT-proBNP comprising a mutation substituting arginine at position 46 with histidine, or an antigen-binding fragment thereof and ii) an antibody that specifically binds a mutated NT-proBNP comprising a mutation substituting glutamic acid at position 43 with aspartic acid, or an antigen-binding fragment thereof, or b) i) an antibody that specifically binds a mutated NT-proBNP comprising a mutation substituting arginine at position 46 with histidine, or an antigen-binding fragment thereof, and ii) an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment thereof or c) i) an antibody that specifically binds a mutated NT-proBNP comprising a mutation substituting glutamic acid at position 43 with aspartic acid, or an antigen-binding fragment thereof, and
ii) an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment thereof, d) i) an antibody that specifically binds a mutated NT-proBNP comprising a mutation substituting arginine at position 46 with histidine, or an antigen-binding fragment thereof, and
ii) an antibody that specifically binds a mutated NT-proBNP comprising a mutation substituting glutamic acid at position 43 with aspartic acid, or an antigen-binding fragment thereof, and
iii) an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment thereof, e) an antibody that specifically binds a mutated NT-proBNP comprising a mutation substituting arginine at position 46 with histidine, or an antigen-binding fragment thereof, or f) an antibody that specifically binds a mutated NT-proBNP comprising a mutation substituting glutamic acid at position 43 with aspartic acid, or an antigen-binding fragment thereof.

Preferably, the antibodies comprised by the kit are monoclonal antibodies. In an embodiment, the antibodies are monoclonal sheep antibodies.

Preferably, the antibodies (or antigen binding fragments thereof) referred to under a), b), c), d), e) or f) of the kit or composition shall comprise a detectable label (for a definition of this term, see elsewhere herein). Thus, each of the antibodies (or antigen binding fragment thereof) as forth under a), b), c), d), e) or f) shall be operably linked to a detectable label. In particular, it is envisaged that the antibodies are bound to an identical label. Preferably, each of the antibodies (or antigen binding fragments thereof) is ruthenylated.

Preferably, the kit or composition of the present invention comprises a further antibody, or an antigen-binding fragment thereof, which binds both the mutated NT-proBNP and the wild-type NT-proBNP. Thus, said antibody (or antigen-binding fragment thereof) shall specifically binds to a different region in NT-proBNP, in particular to a region which does not comprise amino acid 42 to 46 of NT-proBNP. Preferably, said further antibody (or antigen-binding fragment thereof) specifically binds to an epitope present in amino acids 1 to 35 of NT-proBNP (in particular of NT-proBNP having a sequence shown in SEQ ID NO: 3). More preferably said further antibody (or antigen-binding fragment thereof) binds to an epitope comprised within amino acids 27 to 31 of NT-proBNP (in particular of NT-proBNP having a sequence shown in SEQ ID NO: 3). Said antibody can be a monoclonal antibody or polyclonal antibody. Preferably, however, said antibody is a monoclonal antibody. In an embodiment, the further antibody described in this paragraph is a monoclonal mouse antibody.

The further antibody (or antigen-binding fragment thereof) described in the previous is preferably used as a capture antibody (fragment). Said antibody (or antigen-binding fragment thereof) shall be capable of being immobilized on a solid support (such as a plate, bead or tube). Preferably, said further antibody shall capture the mutated NT-proBNP(s) (as set forth elsewhere herein) and the wild-type NT-proBNP. In a preferred embodiment, the further antibody (or fragment thereof) is biotinylated. Thereby, the antibody (or fragment thereof) may bind to a solid support which comprises avidin or streptavidin.

The definitions and explanation given herein above apply mutatis mutandis to the following except if stated otherwise.

Moreover, the present invention relates to a mutated NT-proBNP comprising a mutation as set forth above, or a fragment thereof. The mutated NT-proBNP has been defined herein above in connection with the antibody of the present invention In an embodiment, the present invention relates to a mutated NT-proBNP comprising a mutation substituting arginine at position 46 with histidine, or to a fragment thereof. Said fragment shall comprise the mutation substituting arginine at position 46 with histidine. Accordingly, said fragment shall comprise histidine at a position corresponding to position 46 of SEQ ID NO: 1 (or to position 46 of SEQ ID NO: 3). Preferably, the mutated NT-proBNP referred to in the paragraph comprises an amino acid sequence as shown in SEQ ID NO: 1.

In an alternative embodiment, the present invention relates to a mutated NT-proBNP comprising a mutation substituting glutamic acid at position 43 with aspartic acid, or to a fragment thereof. Said fragment shall comprise the mutation substituting glutamic acid at position 43 with aspartic acid. Accordingly, said fragment shall comprise aspartic acid at a position corresponding to position 43 of SEQ ID NO: 2 (or to position 43 of SEQ ID NO: 3). Preferably, the mutated NT-proBNP referred to in this paragraph comprises an amino acid sequence as shown in SEQ ID NO: 2.

The mutated NT-proBNP of the present invention, or the fragment thereof can be e.g. used for the generation of the antibody of the present invention. Further, the mutated NT-proBNP, or the fragment thereof can be used as a standard or calibrator for assays in which the antibody (or fragments thereof) of the present invention is used for determining the amount of a mutated NT-proBNP as referred to herein. Accordingly, the aforementioned kit of the present invention may further comprise a) a mutated NT-proBNP comprising a mutation substituting arginine at position 46 with histidine, or fragment thereof, or b) a mutated NT-proBNP comprising a mutation substituting glutamic acid at position 43 with aspartic acid, or a fragment thereof.

It is to be understood the mutation comprised by the fragment of the present invention usually will not be at position 43 or 46 of the fragment since the fragment is shorter than the mutated NT-proBNP. Rather, the mutation comprised by the fragment shall be a mutation corresponding to the mutation substituting arginine at position 46 with histidine or to the mutation substituting glutamic acid at position 43 with aspartic acid. Thus, the fragment shall comprise a histidine residue at the position corresponding to position 46 of the wild-type NT-proBNP, or an aspartic acid residue at the position corresponding to position 43 of the wild-type NT-proBNP.

Preferably, the fragment of the present invention has a length of at least seven amino acids, more preferably of at least ten amino acids, and most preferably of a least 15 amino acids. Also preferably, said fragment shall have a length of at least 20 amino acids.

The fragment shall be shorter than the mutated NT-proBNP as referred to above, i.e. shorter than 76 amino acids.

In a preferred embodiment, said fragment of the mutated NT-proBNP has a length of not more than 75 amino acids, or in particular of not more than 70 amino acids. In another preferred embodiment, the fragment has a length of not more than 50 amino acids. It is further envisaged that said fragment has a length of not more than 30 amino acids. Thus, said fragment preferably has length of 7 to 70 amino acids (or 7 to 75 amino acids), 10 to 70 amino acids (or 10 to 75 amino acids), or of 20 to 70 amino acids (or 20 to 75 amino acids). Also preferably, said fragment has a length of 10 to 30 amino acids.

The mutated NT-proBNP or fragment thereof can be advantageously used as antigen for the production of the antibody of the present invention. Moreover, the mutated NT-proBNP or fragment can be used as positive control in the kit of the present invention (see above).

In a preferred embodiment, the fragment comprising the mutation substituting arginine at position 46 with histidine comprises or consists of the sequence as shown in SEQ ID NO: 6. In another preferred embodiment the fragment comprising the mutation substituting arginine at position 46 with histidine comprises or consists of the sequence as shown in SEQ ID NO: 7.

In a preferred embodiment, the fragment comprising the mutation substituting glutamic acid at position 43 with aspartic acid comprises or consists of the sequence as shown in SEQ ID NO: 8. In another preferred embodiment the fragment comprising the mutation substituting glutamic acid at position 43 with aspartic acid comprises or consists of the sequence as shown in SEQ ID NO: 9.

In an embodiment of the present invention, the mutated NT-proBNP or fragment thereof further comprises a purification tag. The tag shall be operably linked to the mutated NT-proBNP or fragment thereof.

The tag shall allow the purification of the NT-proBNP or fragment thereof. Such tags are well known in the art. The term "purification tag" as used herein preferably refers to an additional amino acid sequence (a peptide of polypeptide) which allows for purification of the mutated NT-proBNP of the present invention or fragment thereof. In an embodiment, the purification tag is a peptide or polypeptide which is not naturally linked to the mutated NT-proBNP or fragment thereof. Thus, the purification tag shall be heterologous with respect to the mutated NT-proBNP or fragment thereof.

Preferably, the purification tag is selected from the group consisting of a polyhistidine tag, a polyarginine tag, glutathione-S-transferase (GST), maltose binding protein (MBP), influenza virus HA tag, thioredoxin, staphylococcal protein A tag, the FLAG™ epitope, and the c-myc epitope. In a preferred embodiment, the purification tag is a polyhistidine tag, Preferably, said polyhistidine tag comprises at least 6 consecutive histidine residues.

In an embodiment of the present invention, the mutated NT-proBNP or fragment thereof further comprises a carrier protein. The carrier protein shall be operably linked to the mutated NT-proBNP or fragment thereof.

The carrier protein is preferably heterologous with respect to the mutated NT-proBNP or fragment thereof. Carrier proteins desirably are proteins that elicit an immune response. Thus, a carrier protein shall have a high degree of immunogenicity. Such carrier proteins are well known in the art. Preferably, the carrier protein is selected from the group consisting of keyhole limpet haemocyanin (KLH), tetanus toxoid, and diphtheria toxin, bovine serum albumin (BSA), ovalbumin, and thyroglobulin, especially KLH.

The present invention also relates to a composition, said composition comprising i) the mutated NT-proBNP of the present invention or ii) the fragment of the present invention, and further comprising an immunoadjuvant. The term "immunoadjuvant" as used herein refers to a substance or composition which, when administered together with an antigenic substance to organisms, can enhance immunoresponse to the antigenic substance. Preferred adjuvants are described above. In an embodiment, the immunoadjuvant is selected from alum, Freund's incomplete adjuvant, and in particular Freund's complete adjuvant.

Moreover, the present invention relates to the use of a mutated NT-proBNP of the present invention, or of a fragment thereof for the production of the antibody of the present invention. Preferably, said antibody shall specifically bind to a mutated NT-proBNP as defined elsewhere herein. In an embodiment, said antibody is a monoclonal antibody. Alternatively, the composition defined in the previous paragraph is used for the generation of the antibody.

The present invention further relates to a polynucleotide encoding the mutated NT-proBNP of the present invention, or fragment of the present invention.

The term "polynucleotide" as used herein refers to a linear or circular nucleic acid molecule. It encompasses DNA as well as RNA molecules. The polynucleotide of the present invention shall be provided, preferably, either as an isolated polynucleotide (i.e. isolated from its natural context) or in genetically modified form. The term encompasses single as well as double stranded polynucleotides. Moreover, comprised are also chemically modified polynucleotides including naturally occurring modified polynucleotides such as glycosylated or methylated polynucleotides or artificial modified ones such as biotinylated polynucleotides. The polynucleotide of the present invention is characterized in that it shall encode a polypeptide as referred to above. Due to the degeneracy of the genetic code, polynucleotides are encompassed which encode a specific amino acid sequence as recited above. In an embodiment, the polynucleotide does not comprise intron sequences.

In an embodiment, the polynucleotide of the present invention is operably linked to a promoter. Said promoter shall allow for the expression of the polynucleotide. In an embodiment, said promoter is a heterologous promoter. In addition, the polynucleotide of the present invention may be linked to a terminator.

The present invention also contemplates a vector comprising one of the aforementioned polynucleotide of the present invention. In an embodiment, said vector is an expression vector, in which the polynucleotide of the present invention is operably linked to a promoter, in particular to a heterologous promoter.

The term "vector", preferably, encompasses phage, plasmid, viral or retroviral vectors as well as artificial chromosomes, such as bacterial or yeast artificial chromosomes. More preferably, the vector of the present invention is an expression vector. In such an expression vector, the polynucleotide comprises an expression cassette as specified above allowing for expression in eukaryotic cells or isolated fractions thereof. An expression vector may, in addition to the polynucleotide of the invention, also comprise further regulatory elements including transcriptional as well as translational enhancers. Preferably, the expression vector is also a gene transfer or targeting vector. Expression vectors derived from viruses such as retroviruses, vaccinia virus, adeno-associated virus, herpes viruses, or bovine papilloma virus, may be used for delivery of the polynucleotides of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

The present invention also relates to a host cell comprising the mutated NT-proBNP of the present invention, or the fragment thereof, the polynucleotide of the present invention, or the vector of the present invention.

The term "host cell" as referred to in the previous paragraph shall be prokaryotic or eukaryotic cell. Eukaryotic cells include protist, fungal, plant and animal cells. In another embodiment, host cells include but are not limited to the prokaryotic cell line *E. Coli*; mammalian cell lines CHO, HEK293, COS, NSO, SP2 and PER.C6; the insect cell line Sf9; and the fungal cell Saccharomyces *cerevisiae*. In connection with the present invention, it is also envisaged that the host cell is a non-human host cell. In an embodiment, the mutated NT-proBNP, the fragment, the polynucleotide, or the vector comprised by the host cell of the present invention is heterologous with the respect to the host cell. For example, it is envisaged that the host cell has been transfected with the polynucleotide of the present invention.

Moreover, the present invention relates to a kit or composition comprising:
 (i) a mutated NT-proBNP comprising a mutation substituting arginine at position 46 with histidine, or fragment thereof, or
 (ii) a mutated NT-proBNP comprising a mutation substituting glutamic acid at position 43 with aspartic acid, or a fragment thereof, or
 (iii) a mutated NT-proBNP comprising a mutation substituting arginine at position 46 with histidine, or fragment thereof, and a mutated NT-proBNP comprising a mutation substituting glutamic acid at position 43 with aspartic acid, or a fragment thereof.

The term "fragment" has been explained elsewhere herein. The definitions and explanations apply accordingly.

In an embodiment of the aforementioned kit (or composition), the kit (or composition) further comprises the wild-type NT-proBNP, or a fragment thereof. Preferably, said fragment comprises at least amino acid residues 42 to 46 of the wild-type NT-proBNP. In an embodiment, the fragment has a length of at least 10 amino acids.

Moreover, the present invention relates to a method of diagnosing heart failure in a subject, comprising the steps of:
 a) determining the amount of NT-proBNP in a sample from a subject, and
 b) comparing the amount of NT-proBNP as determined in step a) to a reference amount, thereby diagnosing heart failure.

In a preferred embodiment of the aforementioned method, the determination of the amount of NT-proBNP comprises the step of contacting the sample with at least one antibody (or at least one antigen binding fragment of the antibody) of the present invention. In particular, the determination of NT-proBNP comprises the step of contacting the sample with at least:
(i) an antibody that specifically binds a mutated NT-proBNP comprising a mutation substituting arginine at position 46 with histidine, or an antigen binding fragment thereof, or
(ii) an antibody that specifically binds a mutated NT-proBNP comprising or a mutation substituting glutamic acid at position 43 with aspartic acid, or an antigen binding fragment thereof, or
(iii) an antibody that specifically binds a mutated NT-proBNP comprising a mutation substituting arginine at position 46 with histidine, or an antigen binding fragment thereof, and an antibody that specifically binds a mutated NT-proBNP comprising or a mutation substituting glutamic acid at position 43 with aspartic acid, or an antigen binding fragment thereof.

In an embodiment of step a) the aforementioned method, the sample is further contacted with an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment of said antibody.

Thus, the determination of NT-proBNP comprises the step of contacting the sample with at least:
(i) an antibody that specifically binds a mutated NT-proBNP comprising a mutation substituting arginine at position 46 with histidine, or an antigen binding fragment thereof, and an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment thereof, or
(ii) an antibody that specifically binds a mutated NT-proBNP comprising or a mutation substituting glutamic acid at position 43 with aspartic acid, or an antigen binding fragment thereof, and an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment thereof, or
(iii) an antibody that specifically binds a mutated NT-proBNP comprising a mutation substituting arginine at position 46 with histidine, or an antigen binding fragment thereof, and an antibody that specifically binds a mutated NT-proBNP comprising or a mutation substituting glutamic acid at position 43 with aspartic acid, or an antigen binding fragment thereof, and an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment thereof.

The subject in accordance with the method of the present invention is preferably a human.

In an embodiment, the subject is heterozygous, or in particular homozygous for the mutation in NT-proBNP in which arginine at position 46 is substituted with histidine. Preferably, the antibodies/antigen binding fragments in i) or iii) as set forth above are used.

In an alternative embodiment, the subject is heterozygous, or in particular homozygous for the mutation in NT-proBNP in which glutamic acid at position 43 is substituted with aspartic acid. Preferably, the antibodies/antigen binding fragments in ii) or iii) as set forth above are used.

In an embodiment of the present invention, the sample is a blood, serum, or plasma sample. For example, blood samples, i.e. whole blood samples, can be used for the determination of NT-proBNP in the Point-of-Care setting. The most preferred samples are plasma and serum. Such types of samples are routinely used in laboratory testing.

Moreover, the present invention relates to the use of at least one antibody of the present invention (or at least one antigen-binding fragment thereof) in a sample of a subject (as defined herein above) for diagnosing heart failure. Preferably, the antibody (or the antibodies) as set forth in i), ii), iii) in connection with step a) of the method of diagnosing heart failure is (are) used. In addition to said antibody (antibodies), or antigen binding fragment(s) thereof, it is envisaged an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment of said antibody is used.

The antibodies or antigen binding fragments that are applied in the use or method of the present invention may comprise a detectable label as described elsewhere.

In the following, preferred embodiments of the present invention are summarized. The definitions given in the description above and in the claims apply accordingly.

1. An antibody that specifically binds a mutated NT-proBNP, wherein said antibody is selected from
    (a) an antibody that specifically binds a mutated NT-proBNP comprising a mutation substituting arginine at position 46 with histidine, and
    (b) an antibody that specifically binds a mutated NT-proBNP comprising a mutation substituting glutamic acid at position 43 with aspartic acid.
2. The antibody of embodiment 1, wherein said antibody is a monoclonal antibody.
3. The antibody of embodiment 1 or 2, wherein said antibody is a sheep antibody.
4. The antibody of any one of embodiments 1 to 3, wherein said NT-proBNP is mutated human NT-proBNP.
5. The antibody of any one of embodiments 1 to 4, wherein
    (i) said mutated NT-proBNP comprising a mutation substituting arginine at position 46 with histidine comprises an amino acid sequence as shown in SEQ ID NO: 1, or
    (ii) said mutated NT-proBNP comprising a mutation substituting glutamic acid at position 43 with aspartic acid comprises an amino acid sequence as shown in SEQ ID NO: 2.
6. The antibody of any one of embodiments 1 to 5, wherein said antibody does not significantly bind to wild-type NT-proBNP.
7. The antibody of any one of embodiments 1 to 6, wherein
    i) the antibody specifically binds to mutated NT-proBNP comprising a mutation substituting arginine at position 46 with histidine, and wherein the light chain of said antibody comprises the amino acid sequence of SEQ ID NO: 4 and wherein the heavy chain of said antibody comprises the amino acid sequence of SEQ ID NO: 5, or
    ii) the antibody specifically binds to mutated NT-proBNP comprising a mutation substituting glutamic acid at position 43 with aspartic acid, and wherein the light chain of said antibody comprises the amino acid sequence of SEQ ID NO: 12 and wherein the heavy chain of said antibody comprises the amino acid sequence of SEQ ID NO: 13.
8. An antigen-binding fragment of the antibody of any one of embodiments 1 to 7.
9. The antigen-binding fragment of embodiment 8, wherein the antigen-binding fragment is selected from the group consisting of a Fab fragment, a Fab' fragment, a Facb fragment, a F(ab')₂ fragment, a scFv fragment, and a Fv fragment.
10. The antibody of any one of embodiments 1 to 7, or the antigen-binding fragment of embodiments 8 or 9, wherein said antibody or said antigen-binding fragment is linked to a detectable label.
11. The antibody or antigen-binding fragment of embodiment 10, wherein said detectable label is an enzyme, biotin, a radioactive label, a fluorescent label, a chemiluminescent label, an electrochemiluminescent label, a gold label, or a magnetic label, in particular wherein said detectable label is an electrochemiluminescent label.
12. The antibody or antigen-binding fragment of embodiments 10 or 11, wherein said detectable label comprises ruthenium.
13. A host cell producing the antibody of any one of embodiments 1 to 7, or the antigen-binding fragment of embodiments 8 and 9.
14. A kit or composition comprising
   a) i) an antibody that specifically binds a mutated NT-proBNP comprising a mutation substituting arginine at position 46 with histidine, or an antigen-binding fragment thereof and ii) an antibody that specifically binds a mutated NT-proBNP comprising a mutation substituting glutamic acid at position 43 with aspartic acid, or an antigen-binding fragment thereof, or
   b) i) an antibody that specifically binds a mutated NT-proBNP comprising a mutation substituting arginine at position 46 with histidine, or an antigen-binding fragment thereof, and ii) an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment thereof or
   c) i) an antibody that specifically binds a mutated NT-proBNP comprising a mutation substituting glutamic acid at position 43 with aspartic acid, or an antigen-binding fragment thereof, and ii) an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment thereof, or
   d) i) an antibody that specifically binds a mutated NT-proBNP comprising a mutation substituting arginine at position 46 with histidine, or an antigen-binding fragment thereof, and ii) an antibody that specifically binds a mutated NT-proBNP comprising a mutation substituting glutamic acid at position 43 with aspartic acid, or an antigen-binding fragment thereof, and iii) an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment thereof.
15. The kit or composition of embodiment 14, wherein the antibodies referred to under a), b), c) or d) are bound to a detectable label, preferably to an electrochemiluminescent label, in particular wherein the antibodies are ruthenylated.
16. The kit or composition of any one of embodiments 13 to 15, further comprises an antibody which binds to a different epitope in NT-proBNP, in particular wherein said antibody binds to an epitope present in amino acids 1 to 35 of NT-proBNP.
17. A mutated NT-proBNP comprising
   i) a mutation substituting arginine at position 46 with histidine, or
   ii) a mutation substituting glutamic acid at position 43 with aspartic acid, or a fragment of said mutated NT-proBNP, wherein said fragment comprises
   i) the mutation substituting arginine at position 46 with histidine, or
   ii) the mutation substituting glutamic acid at position 43 with aspartic acid.
18. The mutated NT-proBNP or fragment thereof of embodiment 17, wherein said mutated NT-proBNP comprises a sequence as shown in SEQ ID NO: 1 or SEQ ID NO: 2.
19. The mutated NT-proBNP or fragment thereof of embodiment 17 or 18, wherein said mutated NT-proBNP or fragment is operably linked to a purification tag or to a carrier protein.
20. A polynucleotide encoding the mutated NT-proBNP or the fragment thereof of any one of embodiments 17 to 19.
21. An expression vector comprising the polynucleotide of embodiment 20.
22. A host cell comprising the mutated NT-proBNP or fragment thereof of any one of embodiments 17 to 19 the polynucleotide of embodiment 20, or the expression vector of embodiment 21.
23. A composition comprising, an immunoadjuvant and the mutated NT-proBNP or fragment thereof of any one of embodiments 17 to 19.
24. Use of the mutated NT-proBNP or fragment thereof of any one of embodiments 17 to 19, or of the composition of embodiments 23 for the production of an antibody.
25. A kit or composition comprising:
   (i) a mutated NT-proBNP comprising a mutation substituting arginine at position 46 with histidine, or fragment thereof, or
   (ii) a mutated NT-proBNP comprising a mutation substituting glutamic acid at position 43 with aspartic acid, or a fragment thereof, or
   (iii) a mutated NT-proBNP comprising a mutation substituting arginine at position 46 with histidine, or fragment thereof, and a mutated NT-proBNP comprising a mutation substituting glutamic acid at position 43 with aspartic acid, or a fragment thereof.
26. The kit or embodiment of embodiment 25, further comprising the wild-type NT-proBNP, or a fragment thereof, wherein said fragment comprises at least amino acid residues 42 to 46 of the wild-type NT-proBNP.
27. A method of diagnosing heart failure in a subject, comprising the steps of:
   a) determining the amount of NT-proBNP in a sample from a subject, and
   b) comparing the amount of NT-proBNP as determined in step a) to a reference amount, thereby diagnosing heart failure, wherein the determination of the amount of NT-proBNP comprises the step of contacting the sample with at least:

(i) an antibody that specifically binds a mutated NT-proBNP comprising a mutation substituting arginine at position 46 with histidine, or an antigen binding fragment thereof, or (ii) an antibody that specifically binds a mutated NT-proBNP comprising or a mutation substituting glutamic acid at position 43 with aspartic acid, or an antigen binding fragment thereof, or (iii) an antibody that specifically binds a mutated NT-proBNP comprising a mutation substituting arginine at position 46 with histidine, or an antigen binding fragment thereof, and an antibody that specifically binds a mutated NT-proBNP comprising or a mutation substituting glutamic acid at position 43 with aspartic acid, or an antigen binding fragment thereof.

28. The method of embodiment 27, wherein the sample is further contacted with an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment of said antibody.

All references referred to above are herewith incorporated by reference with respect to their entire disclosure content as well as their specific disclosure content explicitly referred to in the above description.

EXAMPLES

The following Examples shall illustrate the invention. They shall, however, not be construed as limiting the scope of the invention.

Example 1: Production of Recombinant N-Terminal proBNP (1-76) Muteins NTproBNP (1-76) Mutein [R72H] (i.e. a Mutein Comprising the R46H Substitution) and NTproBNP (1-76) Mutein [E69D] (i.e. a Mutein Comprising the E43D Substitution)

The nucleotide sequence of the N-terminal proBNP (amino acid sequence 1-76) was produced by means of genetic synthesis via PCR and the amplified genes were cloned in suitable expression vector (pQE80) allowing an expression with C-terminal Histidine-Tag. To obtain an optimum expression of the gene the DNA sequence was suited to the codons most frequently used in *E. coli*. The translated protein sequence consists of 92 amino acids comprising N-terminal four amino acid sequence MRGS (SEQ ID NO: 29) followed by NTproBNP (1-76), the amino acids GGGS (SEQ ID NO: 30) and 8 histidines:

```
NTproBNP(1-76)Mutein[R72H]: MRGS-NTproBNP(1-76)
[R72H]-GGGSHHHHHHHH (see SEQ ID NO: 27)

NTproBNP(1-76)Mutein[E69D]: MRGS-NTproBNP(1-76)
[E69D]-GGGSHHHHHHHH (see SEQ ID NO: 28)
```

The plasmids were transformed in *E. coli*. The recombinant *E. coli* clones were inoculated in Super Broth (with 100 µg/ml ampicillin) at an OD 600 of 0,2 and induced at an OD600 of 1,0-1,5 with IPTG (Isopropylthiogalactoside; 0.5 mM final concentration). After the induction the cultures were further incubated for 3 hours at 37° C. The cultures were then centrifuged and the cell pellet gathered in 20 mM Na-phosphate buffer, pH 7,5, 500 mM NaCl. After decomposition of the cell suspension via high pressure the suspension was centrifuged and the supernatant applied on Ni-NTA (Nitrilo-triacetate) column. After a washing step with 50 mM Na-phosphate buffer, pH 7,5, 500 mM NaCl, 20 mM Imidazole the histidine-tagged NT-pro BNP proteins were eluted using a linear gradient of increasing concentration of Imidazole (from 20 mM to 500 mM) in 50 mM Na-phosphate buffer, pH 7,5, 500 mM NaCl buffer.

Example 2: Production and Screening for Monoclonal Antibodies Against NTproBNP (1-76) Mutein [R72H] and NTproBNP (1-76) Mutein [E69D]

Sheep were immunized with recombinant NTproBNP (1-76) Mutein [R72H] and with recombinant NTproBNP (1-76) Mutein [E69D]. Freund's complete was used as adjuvant. After four initial immunizations, the immunizations were repeated in monthly intervals. One lymph node of sheep with positive reacting titer was removed under general anaesthesia and pain medication. After the surgical removal single cell preparations were made out of the lymph node tissue. The lymph node lymphocytes and the permanent myeloma cell line 1C10 (Bioventix) were fused with PEG at a ratio of 2:1 and cultured in Dulbecco's Modified Eagle's Medium supplemented with 4.5 mg/ml glucose, 10% fetal calf serum (Hyclone), 100 µmol/L non essential amino acids (Gibco), 5.7 µM azaserine/100 µM hypoxanthine (Sigma), 50 U/ml human Interleukine-6 (Roche), 100 IU/ml penicillin/100 µm/ml streptomycin (Sigma). The fusions were carried out according to the well-known method of Köhler and Millstein (Nature 256, 1975, p. 495-497). Hybridomas secreting antibodies specific for their respective immunogen sequence were finally cloned by single cell deposition using a FACSAria III.

To identify the presence and specificity of antibodies against NTproBNP (1-76) Mutein [R72H] or NTproBNP (1-76) Mutein [E69D] in the culture supernatant of the hybridoma cells the clones were evaluated by means of ELISA according to the following test principles:

a) Reactivity with NTproBNP (1-76) Mutein [R72H]

Streptavidin coated 384-well microtiter plates (Microcoat) were coated with 1 µg/ml biotinylated MAK <NTproBNP> M-18.4.34 IgG-Bi mono (Roche) in incubation buffer (PBS buffer+0,5% Byco C) for 1 hour at room temperature. M-18.4.34 binds to the region comprising amino acids 27 to 31 of SEQ ID NO: 3, e.g. the antibody binds to the mutated NT-proBNPs as set forth herein and to the wild-type. After washing with washing solution (0,9% NaCl+0,05% Tween 20) a further incubation with the antigen NTproBNP (1-76) Mutein [R72H] diluted at 100 ng/ml in the incubation buffer were carried out for 1 hour at room temperature. After further washing step with washing solution the antibody sample incubation (hybridoma supernatants) were carried out with 50 µl/well for 1 hour at room temperature. After a further washing step with washing buffer incubation with the peroxidase-conjugated AffiniPure Donkey Anti-Sheep-IgG(H+I) detection antibody (Jackson Imm.Research) diluted 1:15.000 in incubation buffer were carried out for 1 hour at room temperature. After a further washing step with washing buffer the peroxidase activity was detected by incubation with ABTS (ready-to-use solution, Roche) for 20 minutes at room temperature and the extinction difference was read in mU at 405 nm by means of an ELISA reader.

Positively reacting hybridoma supernatants were then similarly screened for cross-reactivity against NTproBNP (1-76) Mutein [E69D] and the wild type NTproBNP (1-76).

b) Reactivity with NTproBNP (1-76) Mutein [E69D]

Initial ELISA screenings were performed in similar way as described above using NTproBNP (1-76) Mutein [E69D] as antigen. Positively reacting hybridoma supernatants were then screened for cross-reactivity against NTproBNP (1-76) Mutein [R72H] and the wild type NTproBNP (1-76).

Example 3: Characterization of Kinetic Properties of the Monoclonal Antibodies

A T200 instrument was mounted with a Biacore Series S Sensor Chip CM5. The system buffer was 1 mM $KH_2PO_4$, 10 mM $Na_2HPO_4$ pH 7.4, 500 mM NaCl, 2.7 mM KCl, 0.05% Tween 20. In order to determine the velocity factor, the system was incubated at 13° C. and 37° C. The sample buffer was the system buffer, additionally supplemented with 1 mg/ml CMD (Carboxymethyldextran, Fluka). An antibody capture system was established. 5000 RU rabbit anti-sheep polyclonal antibody (Id.: 313-005-045, Dianova) were immobilized at 25° C. at 30 µg/ml in 10 mM sodium acetate buffer pH 5.0, by EDC/NHS coupling as described by the manufacturer. The capture system was regenerated by a 15 sec. wash at 20 µl/min with concentrated HBS buffer (100 mM HEPES pH 7.4, 1.5 M NaCl, 0.05% (w/v) Tween 20) and a 30 sec injection of 100 mM HCl at 20 µl/min followed by a 10 mM glycine buffer pH 1.5 injection for 1 min at 20 µl/min. Antibodies to be captured were injected for 1 min at 10 µl/min at 40 nM concentration diluted in the respective system buffer pH 7.4. After antibody capturing the system was washed by 2.5-fold concentrated system buffer for 30 sec at 60 µl/min followed by 2 min baseline stabilization. Concentration-dependent analyte series were injected in 1:3 dilution steps, from 0.4 nM, 1.1 nM, 3.3 nM, two injections at 10 nM, 30 nM and 90 nM. In another embodiment, the analyte NTproBNP E69D was injected in concentration series from 1.1 nM, 3.3 nM, 10 nM, two injections at 30 nM, 90 nM and 270 nM. The analyte contact time was 5 min and the dissociation time was 10 min. Analyte kinetics were performed at 60 µl/min. Sheep antibodies were captured as ligands on the sensor surface: mAb<NTproBNP(E69D)>S-23.4.66-IgG, mAb<NTproBNP(R72H)>rS-22.2.195-IgG. Roche manufactured analytes were injected in solution: NT-proBNP (aa 1-76) (MW 8.5 kDa); proBNP (aa 27-102) (MW 9.9 kDa); NT-proBNP E69D (MW 10.2 kDa); NT-proBNP R72H (MW 10.2 kDa); system buffer as control; 0-serum SB150610-001. The Biaevaluation software V.3.0 was used according to the instructions of the manufacturer GEHC. A 1:1 binding model with $R_{MAX}$ local was applied to determine kinetic rates.

Figure 1B:
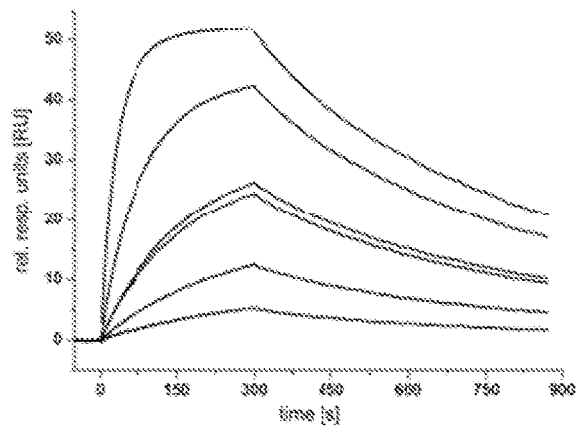
Figure 1B:
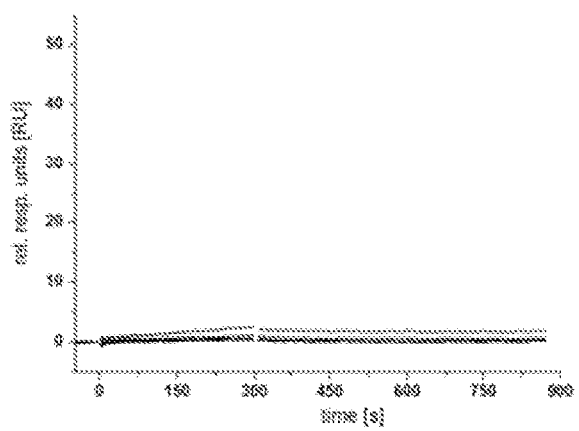
Figure 1B:
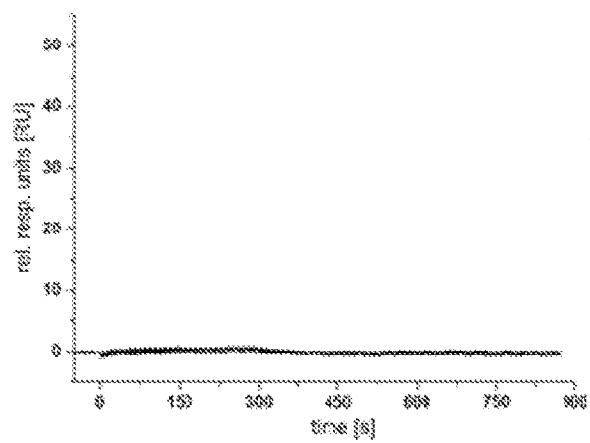
Figure 1B:
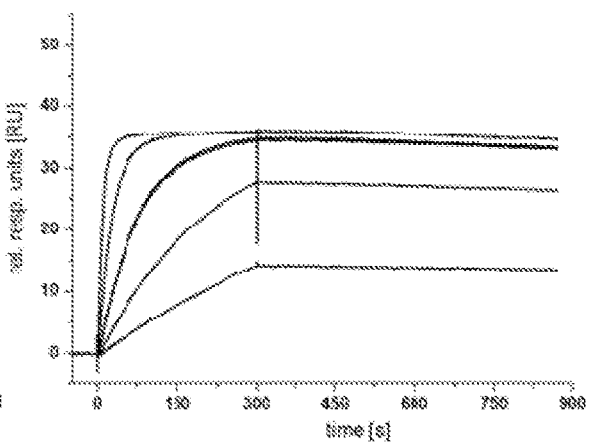

FIGS. 1A and 1B show concentration dependent antibody kinetics performed at 37° C. Antibody S-23.4.66 binds NT-proBNP E69D, but did not show any detectable interaction to full length wild-type NT-proBNP (aa 1-76), wild-type proBNP (aa27-102) and NT-proBNP R72H. The recombinant sheep antibody rS-22.2.195 shows no measureable interactions versus NT-proBNP(aa 1-76), proBNP (aa27-102) and NT-proBNP E69D, but specifically binds to NT-proBNP R72H. Kinetic data are summarized in table 1.

TABLE 1

| mAb | RU | analytes | $k_a$ 1/Ms | $k_d$ 1/s | $t_{1/2}$-diSS min | $K_D$ M | $R_{max}$ RU | MR | Chi² RU² |
|---|---|---|---|---|---|---|---|---|---|
| | | | | 13° C. | | | | | |
| S-23.4.66 | 330 | NTproBNP(1-76)amid | n.d. | n.d. | n.d. | n.d. | 0.6 | n.d. | 0.01 |
| | 314 | proBNP_WT(27-102) | n.d. | n.d. | n.d. | n.d. | 1 | n.d. | 0.02 |
| | 308 | NTproBNP(E69D) | 6.0E+04 | 1.0E−05 | 1144 | 1.7E−10 | 89 | 4.2 | 0.01 |
| | 303 | NTproBNP(R72H) | n.d. | n.d. | n.d. | n.d. | 2 | n.d. | 0.01 |
| rS-22.2.195 | 223 | NTproBNP(1-76)amid | n.d. | n.d. | n.d. | n.d. | 1 | n.d. | 0.04 |
| | 215 | proBNP_WT(27-102) | n.d. | n.d. | n.d. | n.d. | 1 | n.d. | 0.01 |
| | 211 | NTproBNP(E69D) | n.d. | n.d. | n.d. | n.d. | 2 | n.d. | 0.01 |
| | 207 | NTproBNP(R72H) | 4.2E+05 | 1.0E−05 | 1155 | 2.4E−11 | 60 | 4.2 | 0.2 |
| | | | | 25° C. | | | | | |
| S-23.4.66 | 235 | NTproBNP(1-76)amid | n.d. | n.d. | n.d. | n.d. | 1 | n.d. | 0.01 |
| | 230 | proBNP_WT(27-102) | n.d. | n.d. | n.d. | n.d. | 2 | n.d. | 0.01 |
| | 228 | NTproBNP(E69D) | 5.7E+04 | 1.1E−04 | 106 | 1.9E−09 | 49 | 3.1 | 0.02 |
| | 227 | NTproBNP(R72H) | n.d. | n.d. | n.d. | n.d. | 1 | n.d. | 0.01 |
| rS-22.2.195 | 267 | NTproBNP(1-76)amid | n.d. | n.d. | n.d. | n.d. | 1 | n.d. | 0.01 |
| | 258 | proBNP_WT(27-102) | n.d. | n.d. | n.d. | n.d. | 0 | n.d. | 0.01 |
| | 254 | NTproBNP(E69D) | n.d. | n.d. | n.d. | n.d. | 4 | n.d. | 0.01 |
| | 249 | NTproBNP(R72H) | 7.7E+05 | 2.7E−05 | 436 | 3.4E−11 | 46 | 2.7 | 0.00 |
| | | | | 37° C. | | | | | |
| S-23.4.66 | 322 | NTproBNP(1-76)amid | n.d. | n.d. | n.d. | n.d. | 0 | n.d. | 0.01 |
| | 318 | proBNP_WT(27-102) | n.d. | n.d. | n.d. | n.d. | 9 | n.d. | 0.01 |
| | 368 | NTproBNP(E69D) | 1.1E+05 | 1.6E−03 | 7 | 1.5E−08 | 52 | 2.1 | 0.11 |
| | 361 | NTproBNP(R72H) | n.d. | n.d. | n.d. | n.d. | 1 | n.d. | 0.01 |
| rS-22.2.195 | 392 | NTproBNP(1-76)amid | n.d. | n.d. | n.d. | n.d. | 0 | n.d. | 0.01 |
| | 368 | proBNP_WT(27-102) | n.d. | n.d. | n.d. | n.d. | 3 | n.d. | 0.02 |
| | 253 | NTproBNP(E69D) | n.d. | n.d. | n.d. | n.d. | 3 | n.d. | 0.01 |
| | 249 | NTproBNP(R72H) | 1.3E+06 | 8.1E−05 | 143 | 6.4E−11 | 36 | 2.1 | 0.03 | ka:association rate constant [M-1s-1];
kd: dissociation rate constant [s-1];
KD: dissociation constant [M];
t/2diss: halftime of complex dissociation [min] (ln(2)/(kd *60)) [min];
Rmax: maximum analyte binding capacity [RU],
Chi2:statistical fitting model quality;
MR: Molar Ratio, ratio of analyte binding to antibody,
MW(antibody)/MW(antigen) * response (analyte - antibody binding (RU) / antibody capture (RU).
n.d. means not detectable.

In order to estimate the thermodynamic binding properties of the sheep antibodies the temperature-dependent binding kinetic data at 13° C. and 37° C. were used to calculate the Velocity Factor (US20140256915, Table 2). In short, the velocity factor is the quotient of the association rate velocities at ka 37° C. and ka 13° C. If the quotient is below a value of 10, VF<10, the antibody antigen binding is enthalpy dominated, whereas a velocity factor VF >10 increases the likelihood of an entropy-driven kinetic. For matters of specificity and biophysical stability, preferably enthalpy-dominated antibody binding interactions are used for the detection of NT-proBNP wild-type and NT-proBNP mutants in immunological tests.

TABLE 2

| mAb | analytes | VF |
|---|---|---|
| S-23.4.66 | NTproBNP(E69D) | 1.8 |
| rS-22.2.195 | NTproBNP(R72H) | 3.0 |

Example 4: Antibody Sandwich Characterization

Antibody sandwich SPR measurements were conducted at 25° C. A T200 instrument was used as described in example 3 under the same buffer conditions and sensor equipment. 12000 RU RbAMFcg (rabbit anti mouse Fc gamma, PAK<M-Fcg>Rb-IgG(IS), code: 315-005-046, Jackson Immuno Research) were immobilized at 25° C. at 40 µg/ml in 10 mM sodium acetate buffer pH 5.0, by EDC/NHS coupling as described by the manufacturer. The capture system was regenerated by a 15 sec wash at 20 µl/min with concentrated HBS buffer (100 mM HEPES pH 7.4, 1.5 M NaCl, 0.05% (w/v) Tween 20), a 1 min injection of 10 mM glycine buffer pH 1.5 at 20 µmin, followed by two injections for 1 min of 10 mM glycine buffer pH 1.7 at 20 µl/min. 150 nM of the primary murine anti-proBNP antibody M-18.4.34 (27-31) were captured for 1 min at 10 µl/min. Free binding valences of the capture system were saturated by a blocking solution. The blocking solution was injected for 3 min at 30 µl/min followed by 2 min baseline stabilization. The analytes NT-proBNP (aa 1-76) (MW 8.5 kDa); proBNP (aa 27-102) (MW 9.9 kDa) and NT-proBNP R72H (MW 10.2 kDa) were injected at 90 nM for 3 min at 30 µL/min. The analyte NT-proBNP E69D (MW 10.2 kDa) was injected at 180 nM for 3 min at 30 µL/min. In another embodiment instead of recombinant proBNP analytes, human sera were applied as analytes in solution. The sera were diluted 1:5 with sample buffer and were injected at 5 µl/min for 20 min, so that the displayed primary antibody M-18.4.34 (27-31) was saturated by patient serum-derived, native proBNP antigen derivatives. Serum analytes were: 0-serum SB150610-001; NT-proBNP R72H serum; NT-proBNP wild-type serum SE 1053 DI 0580 with 27.39 ng/mL proBNP; In order to evaluate the sandwich performances, 250 nM of each secondary antibody mAb<NTproBNP(E69D)>S-23.4.66-IgG and mAb<NTproBNP(R72H)>rS-22.2.195-IgG SP/Q) were injected at 30 µl/min for 3 min association time and 3 min dissociation time Biaevaluation software V.3.0 was used according to the instructions of the manufacturer GEHC.

Figure 2A:
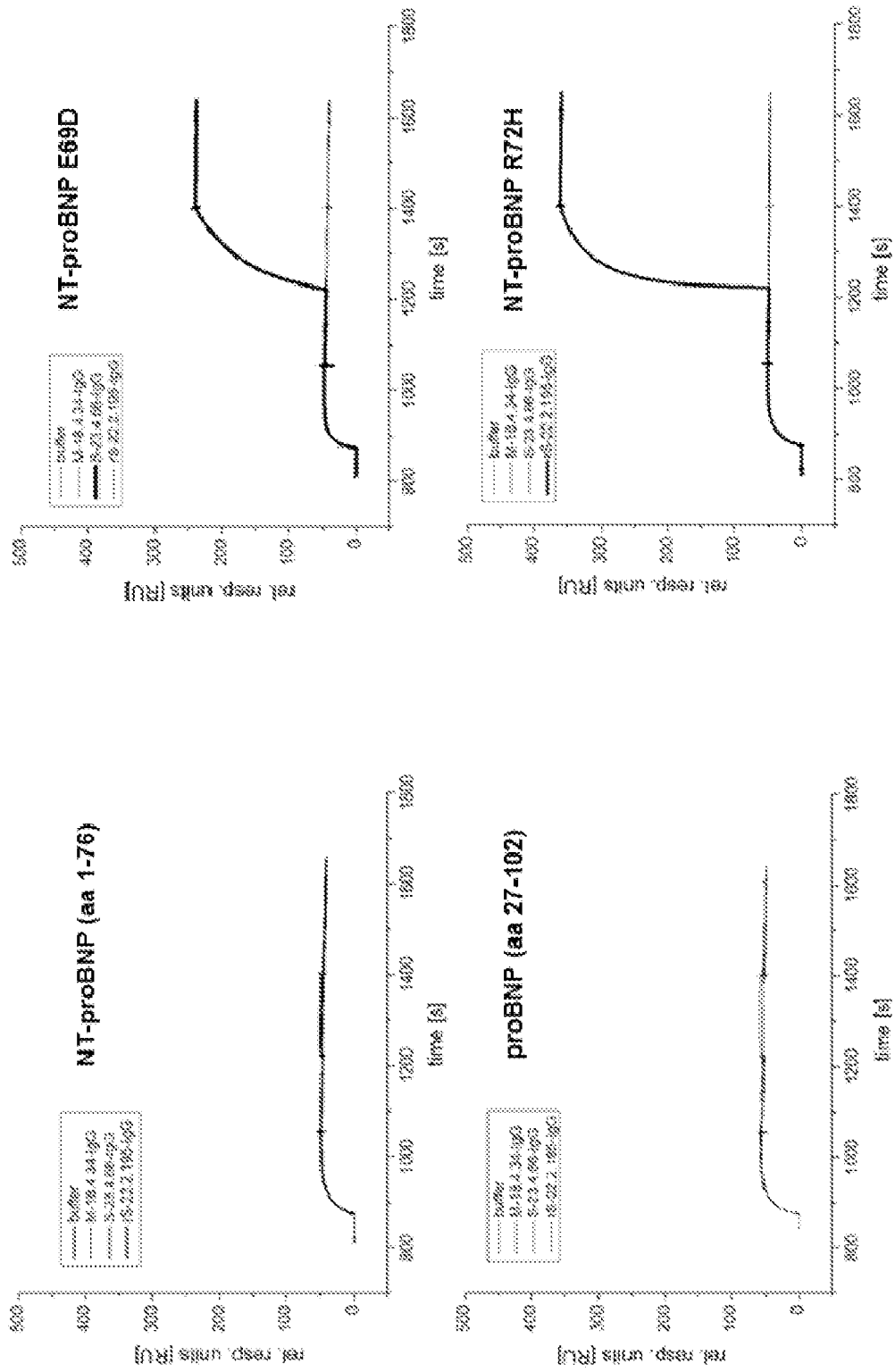
Figure 2B:
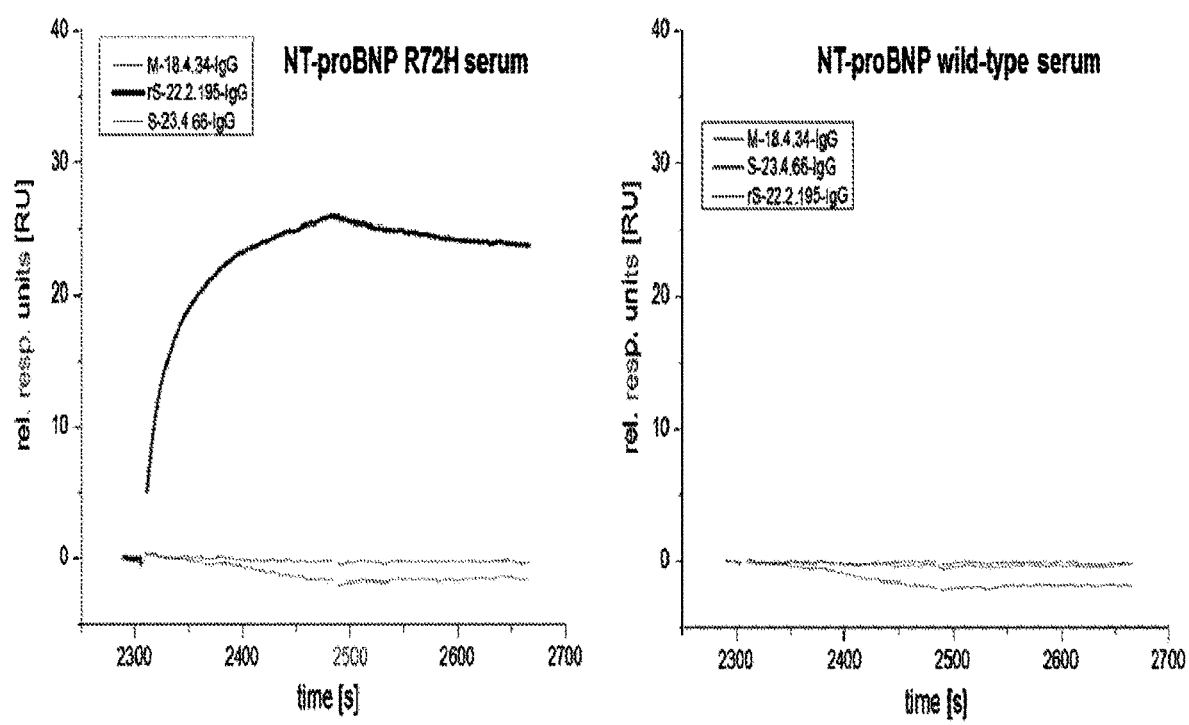

Antibody sandwich experiments with recombinant proBNP and M-18.4.34-IgG as primary antibody and S-23.4.66-IgG or rS-22.2.195-IgG as secondary antibodies are shown in FIGS. 2A and 2B. M-18.4.34-IgG was applied as homologous secondary antibody control. All sensorgrams show analyte saturation of the primary antibody M-18.4.34-IgG, followed by the secondary antibody injections. The primary antibody binds the antigens with high complex stability. rS22.2.195-IgG shows specific complex formation with NT-proBNP R72H. Antibody S-23.4.66-IgG specific complex formation on NT-proBNP E69D.

Similar experiments were performed with human sera instead of recombinant analytes. FIGS. 2A and 2B focus the secondary antibody injections as overlay data. Negative serum (0-serum SB150610-001) was referenced. Antibody rS-22.2.195-IgG forms an antibody sandwich complex specifically with NT-proBNP R72H serum, and no complex formation with wild-type NT-proBNP serum. S-23.4.66-IgG didn't show complex formation within serum samples (NT-proBNP E69D serum is not available).

Example 5: Purification and Ruthenylation of Monoclonal Antibodies rS-22.2.195 and S-23.4.66

Purification of MAK<NTproBNP>S-23.4.66-IgG

A cell-free sheep hybridoma culture supernatant (CELLine, INTEGRA Biosciences AG) is adjusted to pH 4.75 and incubated 30 min at RT. After centrifugation the IgG containing supernatant is supplemented with 0.5 M ammonium sulfate and 150 mM NaCl and the pH is raised to 8.5. The solution is applied to a Protein A-column (ProSep® Ultra Plus, Merck Millipore) and the bound IgG is eluted with 100 mM citrate, 100 mM NaCl, pH 5.5. Following a dialysis against 50 mM K-phosphate, 150 mM NaCl pH 7.5 traces of bovine IgG originating from the FCS in the culture medium are removed using an immunoaffinity resin which specifically binds bovine IgG. The final product is concentrated (Amicon Ultra-30, Merck Millipore), filtered (0.22 µm) and stored at −80° C.

Purification of MAK<NTproBNP>rS-22.2.195-IgG

A cell-free culture supernatant of a CHO cell line expressing the recombinant antibody is adjusted to pH 4.75 and incubated 30 min at RT. After centrifugation the IgG containing supernatant is supplemented with 0.5 M ammonium sulfate and 150 mM NaCl and the pH is raised to 8.5. The solution is applied to a Protein A-column (ProSep® Ultra Plus, Merck Millipore) and the bound IgG was eluted with 100 mM citrate, 100 mM NaCl, pH 5.5. Following a dialysis against 50 mM K-phosphate, 150 mM NaCl pH 7.5 the final product is concentrated (Amicon Ultra-30, Merck Millipore), filtered (0.22 µm) and stored at −80° C.

Ruthenylation of MAK<NTproBNP>S-23.4.66-IgG and MAK<NTproBNP>rS-22.2.195

The Protein A-purified antibodies are dialysed against the ruthenylation buffer (100 mM K-phosphate pH 8.5) and then the solution is adjusted to a protein concentration of 1 mg/ml. Ruthenium(II) tris(bipyridyl)-UEEK-N-hydroxysuccinimide ester is dissolved in DMSO at a concentration >5 mg/ml. A 15-fold molar excess of BPRu-UEEK-DDS is added to the IgG solution and the reaction is performed for 45 minutes at 25° C. while mixing vigorously. The reaction is stopped by adding L-lysin at a final concentration of 10 mM. The excess of the labelling reagent is removed by gel permeation chromatography on Superdex 200 (GE Healthcare Life Sciences) using 100 mM K-phosphate, 150 mM KCl pH 7.5 as running buffer. The fractions containing the conjugated IgG are pooled and the final product is stabilized with 6.5% saccharose and stored at −80° C.

Example 6: Method of Detecting Mutated NT-proBNP

One method to detect NT-proBNP is the well-established Roche Elecsys® assay technology which is based on electrochemiluminescence. The Elecsys® assays are heterogenous immunoassays and function according to the sandwich principle: an antibody-antigen-antibody complex is formed by using a capture and a detection (signal) antibody which were raised against different epitopes of the analyte. An Elecsys® assay to detect mutated NT-proBNP comprises the following steps and components:
  a) The sample is incubated with a monoclonal capture antibody, e.g. M-18.4.34, and with rS-22.2.195, or S-23.4.66, or both as monoclonal signal antibodies in a phosphate-buffered (100 mM, pH 5.8) matrix containing preservatives (Oxy-Pyrion 0.1%, N-Methylisothiazolon 0.1%), a detergent (0.1%), stabilizing and interference-avoiding proteins (e.g. Albumin, Streptavidin-Poly).
  b) The biotinylated capture antibody (e.g. M-18.4.34) and one out of the ruthenium-labeled detection antibodies rS-22.2.195 specific for NT-proBNP-R46H or S-23.4.66 specific for NT-proBNP-E43D form a sandwich complex with the analyte.
  c) The sandwich complex is bound to streptavidin-coated microparticles which are then magnetically captured onto the surface of the electrode.
  d) Unbound substances are removed with ProCell.
  e) Chemiluminescent emission is induced by application of a voltage to the electrode and measured by a photomultiplier.
  f) NT-proBNP values are calculated via a calibration curve which is instrument-specific.

If the Elecsys assay should detect mutated and wild-type NT-proBNP, an additional signal antibody specific for wild-type NT-proBNP, e.g. S-1.21.3, can be included in the assay mixture.

Example 7: Antibodies rS-22.2.195 and S-23.4.66 are Highly Specific for Mutated NT-proBNP The specificity of the two newly generated antibodies, rS-22.2.195 and S-23.4.66, was assessed with an NT-proBNP-specific Elecsys® assay as described in Example 5. Human NT-proBNP-free sera were spiked with a series of recombinant wild-type and mutated peptides so that they cover the range of NT-proBNP concentrations observed in heart failure patients. NT-proBNP in the samples was then detected with either rS-22.2.195 specific for NT-proBNP-R46H (FIG. 3) or S-23.4.66 specific for NT-proBNP-E43D (FIG. 4).

Figure 3:
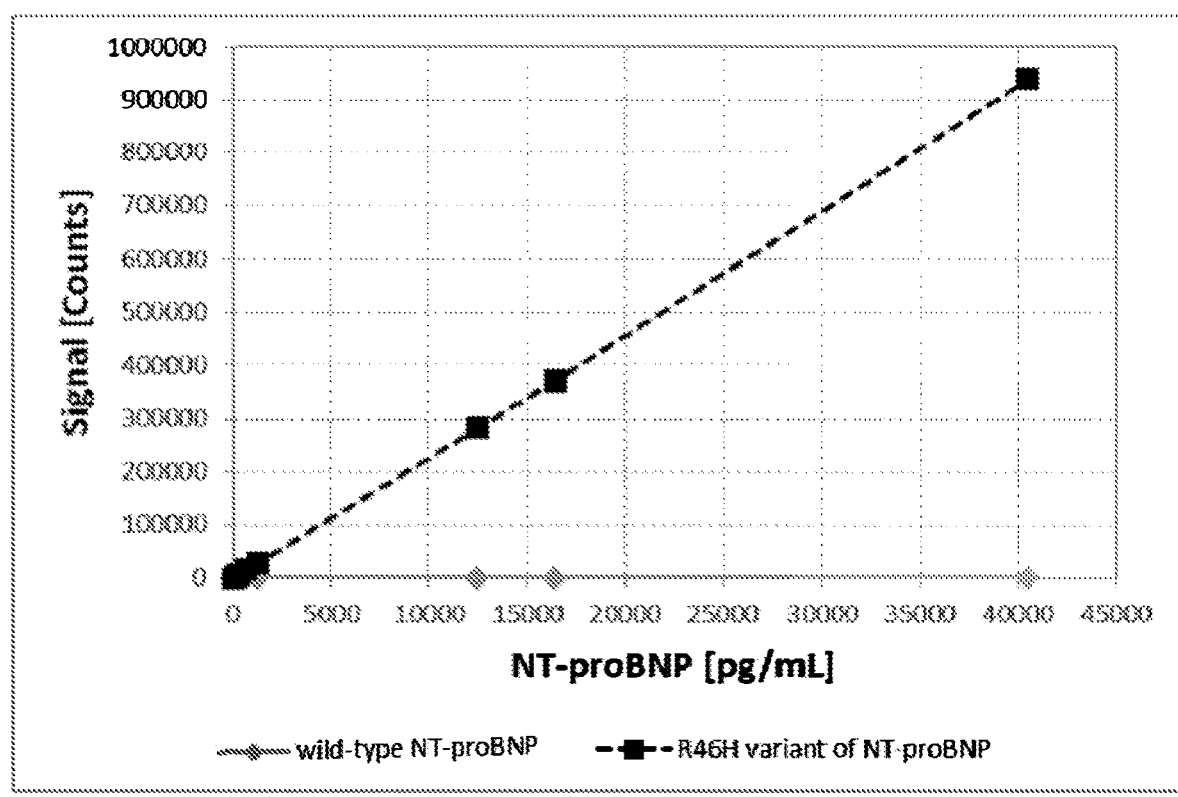
FIG. 3: Specificity of the antibody rS-22.2.195 for NT-proBNP-R46H.
Figure 4:
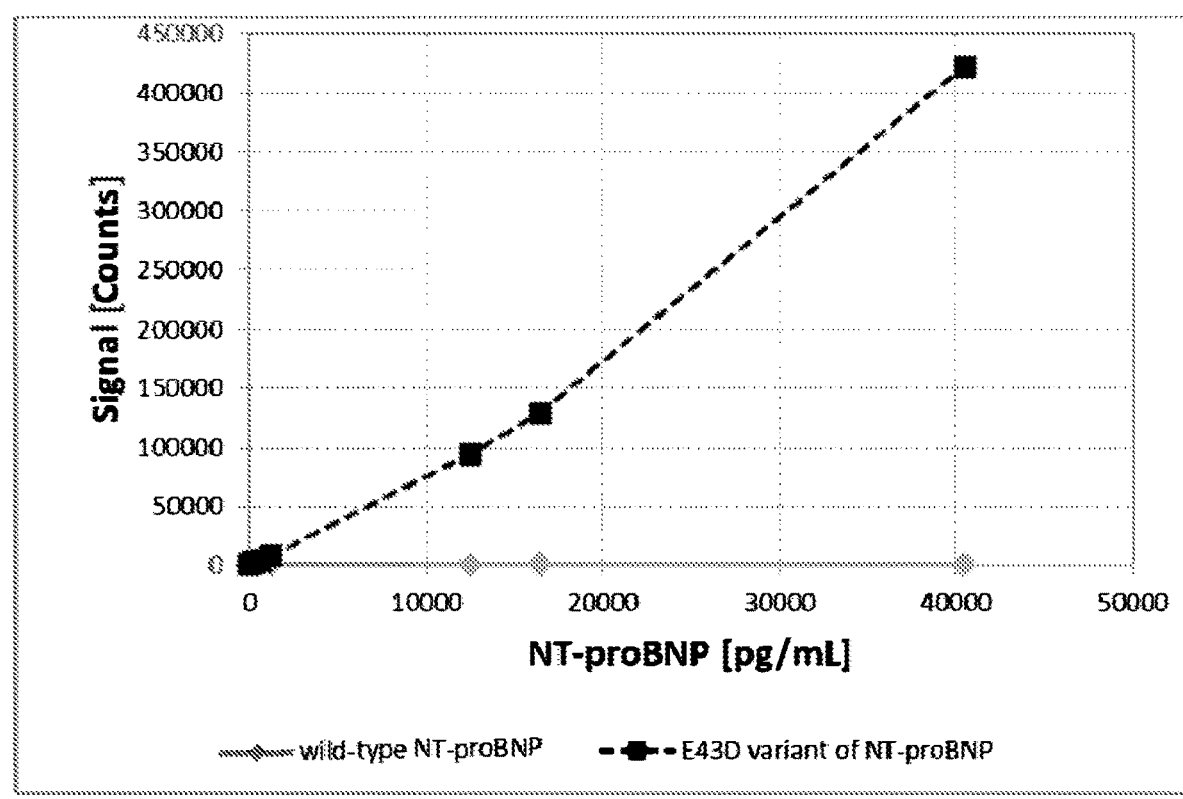
FIG. 4: Specificity of the antibody S-23.4.66 for NT-proBNP-E43D.

The results in FIGS. 3 and 4 show that both antibodies, rS-22.2.195 and S-23.4.66, do not bind to wild-type NT-proBNP at all, but recognize the mutated peptides with high intensity. Furthermore, both antibodies show a wide range of linear correlation of signal vs. analyte concentration and therefore allow quantitation of NT-proBNP across the whole concentration range commonly found in heart failure patients.

Example 8: Reactivity with Mutated NT-proBNP (R46H) in Patient Samples

The reactivity of the new antibodies with native mutated NT-proBNP was assessed in serum or plasma samples from eight patients known to show clear symptoms of heart failure (Table 4, patient 1-8). Only patients with an R46H mutation were available. For three patients, the presence of the R46H mutation was also confirmed by sequencing. NT-proBNP was quantified using the Elecsys® assay system described in example 5 with rS-22.2.195 specific for NT-proBNP-R46H as signal antibody and M-18.4.34 as capture antibody. For comparison, the same patient samples were measured with an Elecsys® kit containing S-23.4.66 specific for NT-proBNP-E43D as signal antibody and M-18.4.34 as capture antibody. Calibration of both assay systems was done with calibrators based on recombinant mutated NT-proBNP (R46H or E43D, respectively).

TABLE 3

| sample name | Target values pg/mL | rS-22.2.195 counts | rS-22.2.195 pg/mL | S-23.4.66 counts | S-23.4.66 pg/mL |
|---|---|---|---|---|---|
| R46H_Cal_1 | 0 | 556 | 0 | | |
| R46H_Cal_2 | 140 | 3538 | 146 | | |
| R46H_Cal_3 | 280 | 6722 | 295 | | |
| R46H_Cal_4 | 625 | 14232 | 638 | | |
| R46H_Cal_5 | 1250 | 27982 | 1254 | | |
| R46H_Cal_6 | 12500 | 294943 | 12543 | | |
| R46H_Cal_7 | 16440 | 382527 | 16149 | | |
| R46H_Cal_8 | 40500 | 993180 | 40801 | | |
| E43D_Cal_1 | 0 | | | 606 | 0 |
| E43D_Cal_2 | 140 | | | 1391 | 193 |
| E43D_Cal_3 | 280 | | | 2094 | 338 |
| E43D_Cal_4 | 625 | | | 4213 | 734 |
| E43D_Cal_5 | 1250 | | | 8349 | 1430 |
| E43D_Cal_6 | 12500 | | | 88292 | 11891 |
| E43D_Cal_7 | 16440 | | | 127133 | 16377 |
| E43D_Cal_8 | 40500 | | | 370954 | 41832 |
| patient 1 | | 96546 | 4229 | 597 | 0 |
| patient 2 * | | 401278 | 16918 | 610 | 0 |
| patient 3 * | | 47570 | 2116 | 611 | 0 |
| patient 4 | | 4730 | 202 | 602 | 0 |
| patient 5 | | 4847 | 207 | 600 | 0 |
| patient 6 * | | 52848 | 2346 | 619 | 3 |
| patient 7 | | 533739 | 22321 | 626 | 6 |
| patient 8 | | 309914 | 13162 | 628 | 7 |

* R46H mutation was confirmed by sequencing

The assay kit containing the rS-22.2.195 antibody clearly detected NT-proBNP-R46H in all patient samples. Control kits using S-23.4.66 as signal antibody did not detect significant amounts of NT-proBNP (≤7 pg/mL). This result again shows the high specificity of rS-22.2.195 and S-23.4.66 for the two point mutations R46H and E43D, respectively, but now also with native samples. The NT-proBNP concentrations quantified with rS-22.2.195 range from 202 to 22321 pg/mL. In the past, the decision threshold for diagnosis of cardiac dysfunction was determined to be 125 pg/mL of (wild-type) NT-proBNP (Roche Elecsys® proBNP II assay). Thus, the measured concentrations of mutated NT-proBNP being all >125 pg/mL might reflect the patients' symptoms of heart failure.

The sequences referred to herein are shown in the sequence listing and in the following table.

TABLE A

Sequences described in the present application

| SEQ ID NO | Brief description | Sequence |
|---|---|---|
| 1 | NT-proBNP with R46H mutation (position 46 indicated in bold) | HPLGSPGSASDLETSGLQEQRNHLQGKLSELQVEQTSLEPLQESHPTGVWKSREVAT EGIRGHRKMVLYTLRAPR |
| 2 | NT-proBNP with E43D mutation (position 43 indicated in bold) | HPLGSPGSASDLETSGLQEQRNHLQGKLSELQVEQTSLEPLQDSPRPTGVWKSREVAT EGIRGHRKMVLYTLRAPR |
| 3 | wild-type NT-proBNP | HPLGSPGSASDLETSGLQEQRNHLQGKLSELQVEQTSLEPLQESPRPTGVWKSREVAT EGIRGHRKMVLYTLRAPR |
| 4 | light chain of antibody S-22.2.195 (CDR1-CDR2-CDR3) indicated in bold (in this order) | 1 YELTQPTSVS VALEQTAEIT CQGDLLDDAY VAWYQQKPGQ APMKLIYKDS <br> 51 ERPSGILDRF SGSSSGKIAT LIISGARTED EADYYCLSVD SSEYSVFGSG <br> 101 TRLTVLSQPK SAPSVTLFPP SKEELDTNKA TVVCLISDFY PGSVNVVWKA <br> 151 DGSTINQNVK TTQASKQSNS KYAASSYLTL TGSEWKSKSS YTCEVTHEGS <br> 201 TVTKTVKPSE CS |
| 5 | heavy chain of antibody S-22.2.195 (CDR1-CDR2-CDR3) indicated in bold (in this order) | 1 QVRLQESGPS LVKPSQTLSL TCTVSGFSLIG EYVTWVRQA PGKAPEWLST <br> 51 MASGGTIFYN PTLKARLSIT KDSTKSQFSL SVSSVTSEDT AMYYCVRSSV <br> 101 SPGDDRDVWG RGLLVTVSSA STTPPKVYPL TSCCGDTSSS IVTLGCLVSS <br> 151 YMPEPVTVTW NSGALTSGVH TFPAILQSSG LYSLSSVVTV PASTSGAQTF <br> 201 ICNVAHPASS TKVDKRVEPG CPDPCKHCRC PPPELPGGPS VFIFPPKPKD <br> 251 TLTISGTPEV TCVVVDVGQD DPEVQFSWFV DNVEVRTART KPREEQFNST <br> 301 FRVVSALPIQ HQDWTGGKEF KCKVHNEGLP APIVRTISRT KGQAREPQVY <br> 351 VLAPPQEELS KSTLSVTCLV TGFYPDYIAV EWQKNGQPES EDKYGTTTSQ <br> 401 LDADGSYFLY SRLRVDKNSW QEGDTYACVV MHEALHNHYT QKSISKPPGK |
| 6 | fragment of NT-proBNP with R46H mutation | ESPHPTG |
| 7 | fragment of NT-proBNP with R46H mutation | QESPHPTGVW |
| 8 | fragment of NT-proBNP with E43D mutation | PLQDSPR |
| 9 | fragment of NT-proBNP with E43D mutation | EPLQDSPRPT |
| 10 | nucleic acid sequence for light chain of antibody S-22.2.195 | 1 tatgaactga cccagccgac ttcagtgtcg gtggccttgg aacagacggc <br> 51 cgaaatcacc tgccaggag atttgttgga tgatgcatat gtggcttgt <br> 101 accagcagaa gccgggccag gctccgatga aactcattta taaagacagt <br> 151 gagcggcctt cagggatcct tgaccggttc tctggctcca gctcaggcaa <br> 201 aatagccacc ctaatcatca gcggggcccg gaccgaggac gaggccgact <br> 251 attactgtct gtcagttgac agcagcgaat attctgtttt cggcagcggg <br> 301 accaggttga ccgttttgag tcagcccaag tccgcaccct cggtcaccct <br> 351 gttcccgcct tccaaggagg agctcgatac caacaaggcc accgtggtgt <br> 401 gtctcatcag cgacttctac ccgggtagcg tgaacgtggt ctggaaggca <br> 451 gatggcagca ccatcaatca gaacgtgaag accacccagg cctccaaaca <br> 501 gagcaacagc aagtacgcgg ccagcagcta cctgaccctg acgggcagcg <br> 551 agtggaagtc taagagcagt tacacctgcg aggtcacgca cgaggggagc <br> 601 accgtgacga agacagtgaa gccctcagag tgttct |
| 11 | nucleic acid sequence for heavy chain of antibody S-22.2.195 | 1 caggtgcggc tgcaggagtc gggacccagc ctggtgaagc cctcacagac <br> 51 cctctcccte acctgcacgg tctctggatt ctcattaatc ggcgagtatg <br> 101 taacctgggt ccgccaggct ccaggaaagg cgccggagtg gctgagtacg <br> 151 atggccagtg gtggaaccat attttataat ccgaccctga aggccgact <br> 201 cagcatcacc aaggacagca ccaagagcca attctccctg tcagtgagca <br> 251 gcgtgacatc tgaggacacg gccatgtatt actgtgtaag atcttccgtt <br> 301 tcaccgggcg atgatagaga tgtctggggc cgaggactcc tggttaccgt <br> 351 ctcctcggcc tccaccacac ccccgaaagt ctaccctctg acttcttgct <br> 401 gcggggacac gtccagctcc atcgtgaccc tgggctgcct ggtctccagc <br> 451 tatatgcccg agccggtgac cgtgacctgg aactctggtg ccctgaccag <br> 501 cggcgtgcac accttccgg ccatcctgca gtcctccggg ctctactctc <br> 551 tcagcagcgt ggtgaccgtg ccggccagca cctcaggagc ccagaccttc <br> 601 atctgcaacg tagcccaccc ggccagcagc accaaggtgg acaagcgtgt <br> 651 tgagcccgga tgcccggacc catgcaaaca ttgccgatgc caccccctg <br> 701 agctccccgg aggaccgtct gtcttcatct tcccaccgaa acccaaggac <br> 751 acccttacaa tctctggaac gccccgaggtc acgtgtgtgg tggtggacgt <br> 801 gggccaggat gaccccgagg tgcagttctc ctggttcgtg gacaacgtgg <br> 851 aggtgcgcac ggccaggaca aagccgagag aggagcagtt caacagcacc <br> 901 ttccgcgtgg tcagcgcct gcccatccag caccaagact ggactggagg <br> 951 aaaggagttc aagtgcaagg tccacaacga ggcctcccg gccccccatcg <br> 1001 tgaggaccat ctccaggacc aaagggcagg cccgggagcc gcaggtgtac <br> 1051 gtcctggccc cacccccagga gagctcagc aaaagcacgc tcagcgtcac <br> 1101 ctgcctggtc accggcttct acccagacta catcgccgtg gagtggcaga <br> 1151 aaaatgggca gcctgagtcg gaggacaagt acggcacgac cacatcccag |

TABLE A-continued

Sequences described in the present application

| SEQ ID NO | Brief description | Sequence |
|---|---|---|
| | | 1201 ctggacgccg acggctccta cttcctgtac agcaggctca gggtggacaa |
| | | 1251 gaacagctgg caagaaggag acacctacgc gtgtgtggtg atgcacgagg |
| | | 1301 ctctgcacaa ccactacaca cagaagtcga tctctaagcc tccgggtaaa |
| 12 | light chain of antibody S-23.4.66 (CDR1-CDR2-CDR3) indicated in bold (in this order) | 1 QAVLTQPSSV SRSPGQSVSI TCSGSSSNVG YGNYVGWFQQ VPGSAPKLLI<br>51 YSATSRASGV PDRFSGSRAG NTATLTITSL QAEDEADYYC VSYDSSSKFG<br>101 VFGSGTRLTV LGQPKSAPSV TLFPPSTEEL STNKATVVCL INDFYPGSVN<br>151 VVWKADGSTI NQNVKTTQAS KQSNSKYAAS SYLTLTGSEW KSKSSYTCEV<br>201 THEGSTVTKT VKPSECS |
| 13 | heavy chain of antibody S-23.4.66 (CDR1-CDR2-CDR3) indicated in bold (in this order) | 1 QVRMQELGPS LVKPSQTLSL TCTVSGFSVT NSGVGWVRQA PGKALEWLGI<br>51 INNDGVAGYN PALKTRLSIT RDTSKNQVSL SLSSVTTEDT AVYYCGTRDL<br>101 PSDVRYGNMY INYWGPGRMV TVSSASTTPP KVYPLTSCCG DTSSSIVTLG<br>151 CLVSSYMPEP VTVTWNSGAL TSGVHTFPAI LQSSGLYSLS SVVTVPASTS<br>201 GAQTFICNVA HPASSTKVDK RVEPGCPDPC KHCRCPPPEL PGGPSVFIFP<br>251 PKPKDTLTIS GTPEVTCVVV DVGQDDPEVQ FSWFVDNVEV RTARTKPREE<br>301 QFNSTFRVVS ALPIQHQDWT GGKEFKCKVH NEGLPAPIVR TISRTKGQAR<br>351 EPQVYVLAPP QEELSKSTLS VTCLVTGFYP DYIAVEWQKN GQPESEDKYG<br>401 TTTSQLDADG SYFLYSRLRV DKNSWQEGDT YACVVMHEAL HNHYTQKSIS<br>451 KPPGK |
| 14 | nucleic acid sequence for light chain of antibody S-23.4.66 | 1 caggctgtgc tgactcagcc gtcctccgtg tccaggtccc cgggccagag<br>51 tgtctccatc acctgctctg gaagcagcag caacgttgga tatggtaatt<br>101 atgtgggctg gttccaacaa gtcccaggat cagccccaa actcctcatc<br>151 tatagtgcga cccagtcgag ctcggggtc cccgaccgat tctccggctc<br>201 cagggctggc aacacagcga ccctgaccat cacttcgctc caggctgagg<br>251 acgaggccga ttattattgt gtatcttatg acagtagtag caaatttggt<br>301 gttttcggca gcgggaccag gctgaccgtc ctgggtcagc ccaagtccgc<br>351 accctcggtc accctgttcc cgccttccac ggaggagctc agtaccaaca<br>401 aggccaccgt ggtgtgtctc atcaacgact ctacccggg tagcgtgaac<br>451 gtggtctgga aggcagatgg cagcaccatc aatcagaacg tgaagaccac<br>501 ccaggcctcc aaacagagca acagcaagta cgcggccagc agctacctga<br>551 ccctgacggg cagcgagtgg aagtctaaga gcagttacac ctgcgaggtc<br>601 acgcacgagg ggagcaccgt gacgaagaca gtgaagccct cagagtgttc<br>651 t |
| 15 | nucleic acid sequence for heavy chain of antibody S-23.4.66 | 1 caggtgcgga tgcaggagtt gggacccagc ctggtgaagc cctcacagac<br>51 cctctccctc acgtgcacgg tctctggatt ctcagtaacc aacagtggtg<br>101 taggctgggt ccgccaggct ccaggaaagg ccctggagtg gcttggtatt<br>151 ataaataatg atggagtcgc aggctataac ccagcccta agacccggct<br>201 cagcatcacc agggacacct ccaagaacca agtctccctg tcattgagca<br>251 gcgtgacaac tgaggacacg gccgtgtact actgtggaac acgagatttg<br>301 cccagtgatg ttcgttatgg aacatgtat atcaactact ggggcccagg<br>351 acgaatggtc accgtctcct cagcctccac cacaccccg aaagtctacc<br>401 ctctgacttc ttgctgcggg gacacgtcca gctccatcgt gaccctgggc<br>451 tgcctggtct ccagctatat gcccgagccg gtgaccgtga cctggaactc<br>501 tggtgccctg accagcggcg tgcacacctt cccggccatc ctgcagtcct<br>551 ccgggctcta ctctctcagc agcgtggtga ccgtgccggc agcacctca<br>601 ggagcccaga ccttcatctg caacgtagcc cacccggca gcagcaccaa<br>651 ggtggacaag cgtgttgagc ccggatgccc ggacccatgc aaacattgcc<br>701 gatgcccacc ccctgagctc cccggaggac cgtctgtctt catcttccca<br>751 ccgaaaccca aggacaccct acaatctct ggaacgcccg aggtcacgtg<br>801 tgtggtggtg gacgtgggcc aggatgaccc cgaggtgcag ttctcctggt<br>851 tcgtggacaa cgtggaggtg cgcacggcca ggcaaaagcc gagagaggag<br>901 cagttcaaca gcaccttccg cgtggtcagc gccctgccca tccagcacca<br>951 agactggact ggaggaaagg agttcaagtg caaggtccac aacgaaggcc<br>1001 tcccggcccc catcgtgagg accatctcca ggaccaaagg gcaggcccgg<br>1051 gagccgcagg tgtacgtcct ggcccacc caggaagagc tcagcaaaag<br>1101 cacgctcagc gtcacctgcc tggtcaccgg cttctaccca gactacatcg<br>1151 ccgtggagtg gcagaaaaat gggcagcctg agtcggagga caagtacggc<br>1201 acgaccacat cccagctgga cgccgacggc tcctacttcc tgtacagcag<br>1251 gctcagggtg gacaagaaca gctggcaaga aggagacacc tacgcgtgtg<br>1301 tggtgatgca cgaggctctg cacaaccact acacacagaa gtcgatctct<br>1351 aagcctccgg gtaaa |
| 16 | CDR1, light chain, antibody S-22.2.195<br>CDR2, light chain, antibody S-22.2.195 | LLDDAY<br>KDS |
| 17 | CDR3, light chain, antibody S-22.2.195 | LSVDSSEYSV |
| 18 | CDR1, heavy chain, antibody S-22.2.195 | GFSLIGEY |

TABLE A-continued

Sequences described in the present application

| SEQ ID NO | Brief description | Sequence |
|---|---|---|
| 19 | CDR2, heavy chain, antibody S-22.2.195 | MASGGTI |
| 20 | CDR3, heavy chain, antibody S-22.2.195 | VRSSVSPGDDRDV |
| 21 | CDR1, light chain, antibody S-23.4.66 | SSNVGYGNY |
|  | CDR2, light chain, antibody S-23.4.66 | SAT |
| 22 | CDR3, light chain, antibody S-23.4.66 | VSYDSSSKFGV |
| 23 | CDR1, heavy chain, antibody S-23.4.66 | GFSVTNSG |
| 24 | CDR2, heavy chain, antibody S-23.4.66 | INNDGVA |
| 25 | CDR3, heavy chain, antibody S-23.4.66 | GTRDLPSDVRYGNMYINY |
| 26 | NT-proBNP with R46H mutation with additional sequences such as His tag | MRGSHPLG SPGSASDLET SGLQEQRNHL QGKLSELQVE QTSLEPLQES PRPTGVWKSR EVATEGIRGH RKMVLYTLRA PRGGGS HHHH HHHH |
| 27 | NT-proBNP with R46H mutation with additional sequences such as His tag | HPLG SPGSASDLET SGLQEQRNHL QGKLSELQVE QTSLEPLQES PHPTGVWKSR EVATEGIRGH RKMVLYTLRA PRGGGSHHHH HHHH |
| 28 | NT-proBNP with E43D mutation with additional sequences such as His tag | MRGSHPLG SPGSASDLET SGLQEQRNHL QGKLSELQVE QTSLEPLQDS PRPTGVWKSR EVATEGIRGH RKMVLYTLRA PRGGGSHHHH HHHH |

The invention claimed is:

1. An antibody that specifically binds a mutated NT-proBNP (N-terminal of the prohormone brain natriuretic peptide), wherein said antibody is selected from
   (a) an antibody that specifically binds a mutated NT-proBNP comprising a mutation substituting arginine at position 46 with histidine, and wherein the light chain variable domain of the antibody comprises a CDR1 having the sequence LLDDAY (SEQ ID NO: 16), a CDR2 having the sequence KDS, and a CDR3 having the sequence LSVDSSEYSV (SEQ ID NO: 17), and the heavy chain variable domain comprises a CDR1 having the sequence GFSLIGEY (SEQ ID NO: 18), a CDR2 having the sequence MASGGTI (SEQ ID NO: 19), and a CDR3 having the sequence VRSSVSPGDDRDV (SEQ ID NO: 20), and
   (b) an antibody that specifically binds a mutated NT-proBNP comprising a mutation substituting glutamic acid at position 43 with aspartic acid, and wherein the light chain variable domain of the antibody comprises a CDR1 having the sequence SSNVGYGNY (SEQ ID NO: 21), a CDR2 having the sequence SAT, and a CDR3 having the sequence VSYDSSSKFGV (SEQ ID NO: 22), and the heavy chain variable domain comprises a CDR1 having the sequence GFSVTNSG (SEQ ID NO: 23), a CDR2 having the sequence INNDGVA (SEQ ID NO: 24), and a CDR3 having the sequence GTRDLPSDVRYGNMYINY (SEQ ID NO: 25).

2. The antibody of claim 1, wherein said antibody is a monoclonal antibody.

3. The antibody of claim 2, wherein the antibody is a monoclonal sheep antibody.

4. The antibody of claim 1, wherein said NT-proBNP is mutated human NT-proBNP, and/or wherein
   (i) said mutated NT-proBNP comprising a mutation substituting arginine at position 46 with histidine comprises an amino acid sequence as shown in SEQ ID NO: 1, or
   (ii) said mutated NT-proBNP comprising a mutation substituting glutamic acid at position 43 with aspartic acid comprises an amino acid sequence as shown in SEQ ID NO: 2.

5. The antibody of claim 1, wherein said antibody does not bind to wild-type NT-proBNP.

6. The antibody of claim 1, wherein said antibody is linked to a detectable label.

7. The antibody of claim 6, wherein said detectable label is an enzyme, biotin, a radioactive label, a fluorescent label, a chemiluminescent label, an electrochemiluminescent label, a gold label, or a magnetic label.

8. The antibody of claim 6 wherein said detectable label is an electrochemiluminescent label comprising ruthenium.

9. An antigen-binding fragment of the antibody of claim 1, wherein the antigen-binding fragment is selected from the group consisting of a Fab fragment, a Fab' fragment, a Facb fragment, a F(ab')$_2$ fragment, a scFv fragment, and a Fv fragment.

10. The antigen-binding fragment of claim 9, wherein said antigen-binding fragment is linked to a detectable label.

11. The antigen-binding fragment of claim 10, wherein said detectable label is an enzyme, biotin, a radioactive label, a fluorescent label, a chemiluminescent label, an electrochemiluminescent label, a gold label, or a magnetic label.

12. A kit or composition comprising
   a) i) an antibody that specifically binds a mutated NT-proBNP comprising a mutation substituting arginine at position 46 with histidine, or an antigen-binding fragment thereof, wherein the light chain variable domain of the antibody comprises a CDR1 having the sequence LLDDAY (SEQ ID NO: 16), a CDR2 having the sequence KDS, and a CDR3 having the sequence LSVDSSEYSV (SEQ ID NO: 17), and the heavy chain variable domain comprises a CDR1 having the sequence GFSLIGEY (SEQ ID NO: 18), a CDR2 having the sequence MASGGTI (SEQ ID NO: 19), and a CDR3 having the sequence VRSSVSPGDDRDV (SEQ ID NO: 20), and
   ii) an antibody that specifically binds a mutated NT-proBNP comprising a mutation substituting glutamic acid at position 43 with aspartic acid, or an antigen-binding fragment thereof, wherein the light chain variable domain of the antibody comprises a CDR1 having the sequence SSNVGYGNY (SEQ ID NO: 21), a CDR2 having the sequence SAT, and a CDR3 having the sequence VSYDSSSKFGV (SEQ ID NO: 22), and the heavy chain variable domain comprises a CDR1 having the sequence GFSVTNSG (SEQ ID NO: 23), a CDR2 having the sequence INNDGVA (SEQ ID NO: 24), and a CDR3 having the sequence GTRDLPSDVRYGNMYINY (SEQ ID NO: 25) or b) i) an antibody that specifically binds a mutated NT-proBNP comprising a mutation substituting arginine at position 46 with histidine, or an antigen-binding fragment thereof, wherein the light chain variable domain of the antibody comprises a CDR1 having the sequence LLDDAY (SEQ ID NO: 16), a CDR2 having the sequence KDS, and a CDR3 having the sequence LSVDSSEYSV (SEQ ID NO: 17), and the heavy chain variable domain comprises a CDR1 having the sequence GFSLIGEY (SEQ ID NO: 18), a CDR2 having the sequence MASGGTI (SEQ ID NO: 19), and a CDR3 having the sequence VRSSVSPGDDRDV (SEQ ID NO: 20), and ii) an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment thereof or c) i) an antibody that specifically binds a mutated NT-proBNP comprising a mutation substituting glutamic acid at position 43 with aspartic acid, or an antigen-binding fragment thereof, wherein the light chain variable domain of the antibody comprises a CDR1 having the sequence SSNVGYGNY (SEQ ID NO: 21), a CDR2 having the sequence SAT, and a CDR3 having the sequence VSYDSSSKFGV (SEQ ID NO: 22), and the heavy chain variable domain comprises a CDR1 having the sequence GFSVTNSG (SEQ ID NO: 23), a CDR2 having the sequence INNDGVA (SEQ ID NO: 24), and a CDR3 having the sequence GTRDLPSDVRYGNMYINY (SEQ ID NO: 25), and ii) an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment thereof, or d) i) an antibody that specifically binds a mutated NT-proBNP comprising a mutation substituting arginine at position 46 with histidine, or an antigen-binding fragment thereof, wherein the light chain variable domain of the antibody comprises a CDR1 having the sequence LLDDAY (SEQ ID NO: 16), a CDR2 having the sequence KDS, and a CDR3 having the sequence LSVDSSEYSV (SEQ ID NO: 17), and the heavy chain variable domain comprises a CDR1 having the sequence GFSLIGEY (SEQ ID NO: 18), a CDR2 having the sequence MASGGTI (SEQ ID NO: 19), and a CDR3 having the sequence VRSSVSPGDDRDV (SEQ ID NO: 20), and ii) an antibody that specifically binds a mutated NT-proBNP comprising a mutation substituting glutamic acid at position 43 with aspartic acid, or an antigen-binding fragment thereof, wherein the light chain variable domain of the antibody comprises a CDR1 having the sequence SSNVGYGNY (SEQ ID NO: 21), a CDR2 having the sequence SAT, and a CDR3 having the sequence VSYDSSSKFGV (SEQ ID NO: 22), and the heavy chain variable domain comprises a CDR1 having the sequence GFSVTNSG (SEQ ID NO: 23), a CDR2 having the sequence INNDGVA (SEQ ID NO: 24), and a CDR3 having the sequence GTRDLPSDVRYGNMYINY (SEQ ID NO: 25), and iii) an antibody that specifically binds to wild-type NT-proBNP, wherein the antibody specifically binds to a region of the wild-type NT-proBNP comprising amino acid residues 42 to 46 of the wild-type NT-proBNP, or an antigen-binding fragment thereof.

13. The kit or composition of claim 12 further comprising an antibody which binds to an epitope comprising amino acids 27 to 31 of NT-proBNP having a sequence shown in SEQ ID NO: 3.

* * * * *